US010376202B2

(12) United States Patent
Shah et al.

(10) Patent No.: US 10,376,202 B2
(45) Date of Patent: *Aug. 13, 2019

(54) SLEEP APNEA AND ANTI-SNORING SYSTEM

(71) Applicant: Real 3D Polymers Group LLC, Troy, MI (US)

(72) Inventors: Nidhi Shah, Chicago, IL (US); Sureshkumar Shah, Troy, MI (US); Dinesh Shah, Troy, MI (US); Shail Chokhavatia, Paramus, NJ (US)

(73) Assignee: Real 3D Polymers Group LLC, Troy, MI (US)

( * ) Notice: Subject to any disclaimer, the term of this patent is extended or adjusted under 35 U.S.C. 154(b) by 490 days.

This patent is subject to a terminal disclaimer.

(21) Appl. No.: 15/383,486

(22) Filed: Dec. 19, 2016

(65) Prior Publication Data

US 2017/0312117 A1 Nov. 2, 2017

Related U.S. Application Data

(60) Provisional application No. 62/269,331, filed on Dec. 18, 2015.

(51) Int. Cl.
*A61B 5/00* (2006.01)
*A61B 5/11* (2006.01)
(Continued)

(52) U.S. Cl.
CPC .............. *A61B 5/4818* (2013.01); *A61B 5/01* (2013.01); *A61B 5/038* (2013.01); *A61B 5/087* (2013.01);
(Continued)

(58) Field of Classification Search
CPC ..... A61F 5/566; A61B 5/0878; A61B 5/4818; A61B 5/4836; A61B 5/4815; A61B 5/002; A61B 5/02055; A61B 5/682; A61B 5/024; A61B 5/0476; A61B 5/0402; A61B 5/1113; A61M 16/0066; A61M 16/049; A61M 16/0468; A61M 16/0069; A61M 2230/50; A61M 16/0493; A61M 2205/3375;
(Continued)

(56) References Cited

U.S. PATENT DOCUMENTS

2005/0236003 A1* 10/2005 Meader .................. A61F 5/566
128/848
2006/0112962 A1* 6/2006 Tebbutt ............. A61M 16/0488
128/206.29
(Continued)

FOREIGN PATENT DOCUMENTS

WO WO 2014/110432 A1 7/2014

OTHER PUBLICATIONS

International Search Report for PCT/US 2016/067543, dated Apr. 6, 2017.

*Primary Examiner* — Tarla R Patel
(74) *Attorney, Agent, or Firm* — Lorenz & Kopf, LLP

(57) ABSTRACT

A sleep apnea treatment/anti-snoring device optionally having controlled positive air-flow using a micro-blower to maintain an individual's upper airway unobstructed (pharynx area). Optionally the device includes a lower jaw mandibular advancement component. The device has built-in sensors, microprocessor and other items required for data acquisition and transfer.

20 Claims, 29 Drawing Sheets

(51) Int. Cl.

| | |
|---|---|
| *A61F 5/56* | (2006.01) |
| *A61B 5/024* | (2006.01) |
| *A61B 5/087* | (2006.01) |
| *A61M 16/00* | (2006.01) |
| *A61M 16/04* | (2006.01) |
| *A61B 5/0205* | (2006.01) |
| *A61B 5/0402* | (2006.01) |
| *A61B 5/0476* | (2006.01) |
| *A61N 1/05* | (2006.01) |
| *A61B 5/01* | (2006.01) |
| *A61B 5/03* | (2006.01) |
| *A61B 5/1455* | (2006.01) |

(52) U.S. Cl.
CPC ........ *A61B 5/14552* (2013.01); *A61B 5/4836* (2013.01); *A61B 5/682* (2013.01); *A61F 5/566* (2013.01); *A61M 16/0069* (2014.02); *A61M 16/024* (2017.08); *A61N 1/0548* (2013.01); *A61B 2562/12* (2013.01); *A61M 16/049* (2014.02); *A61M 16/0493* (2014.02); *A61M 2016/0027* (2013.01); *A61M 2016/0036* (2013.01); *A61M 2205/332* (2013.01); *A61M 2205/3375* (2013.01); *A61M 2205/3584* (2013.01); *A61M 2205/3592* (2013.01); *A61M 2207/00* (2013.01); *A61M 2230/205* (2013.01); *A61M 2230/50* (2013.01)

(58) Field of Classification Search
CPC .. A61M 2016/0027; A61M 2205/3592; A61M 2205/332; A61M 2016/0036; A61M 2205/3584; A61M 2207/00; A61M 2230/205
See application file for complete search history.

(56) References Cited

U.S. PATENT DOCUMENTS

| | | | |
|---|---|---|---|
| 2010/0163043 A1 | 7/2010 | Hart et al. | |
| 2013/0298905 A1* | 11/2013 | Levin | A24F 47/008 128/202.21 |
| 2014/0276171 A1* | 9/2014 | Hestness | A61B 5/097 600/531 |
| 2015/0157492 A1* | 6/2015 | Vaska | A61F 5/566 128/847 |

* cited by examiner

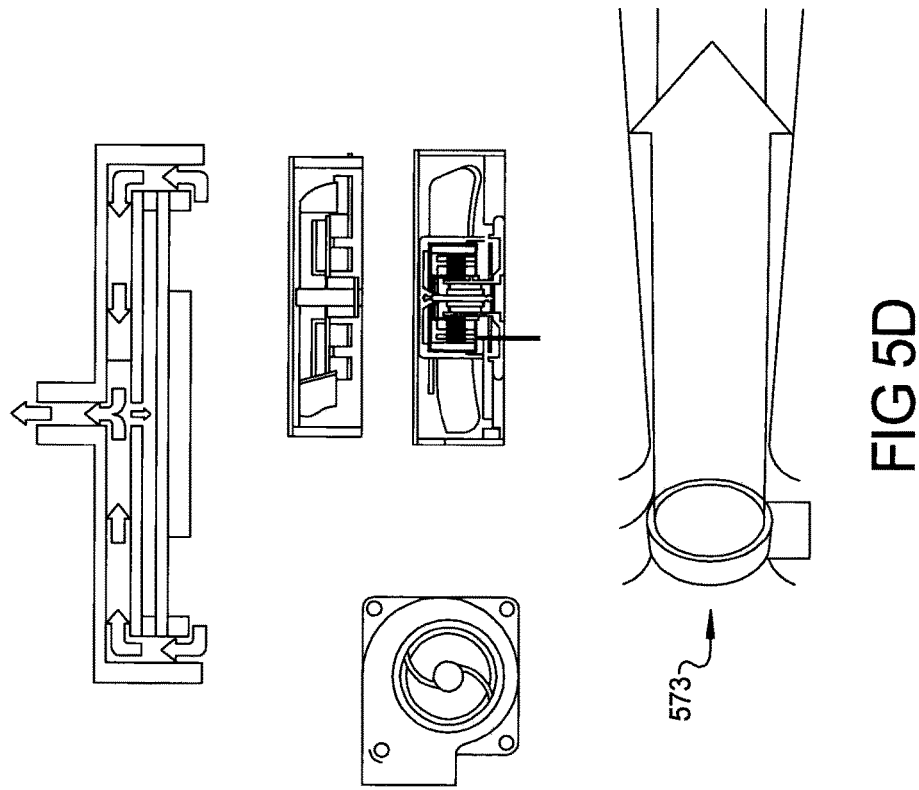
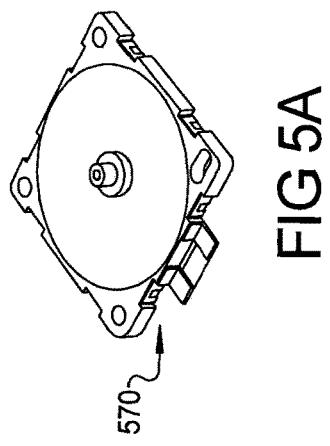
FIG 5A
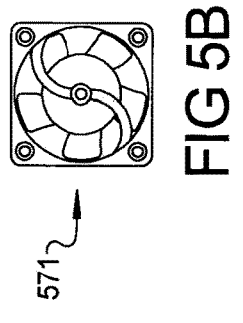
FIG 5B
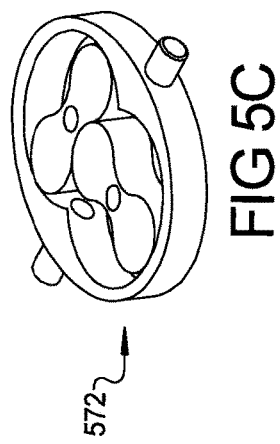
FIG 5C
FIG 5D

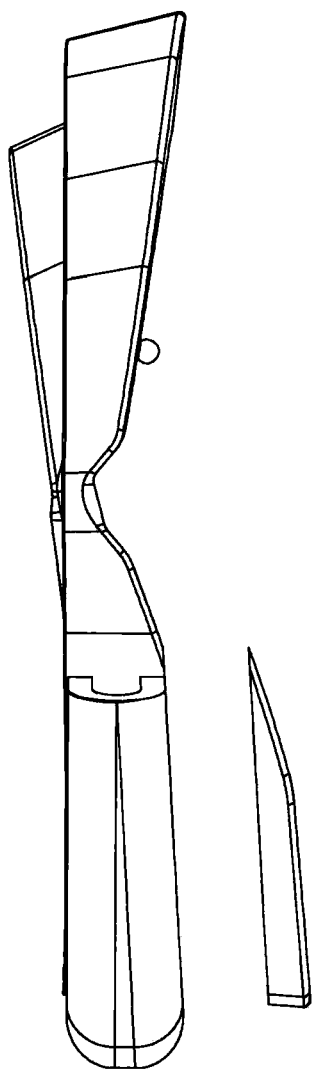
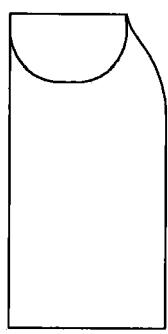
FIG 11

Both non-customized and customized devices consist of two pieces A and B, which are snap-fitted together to produce device

---

Front hollow housing A is made by injection molding with elastomeric ring either inserted or by two shot molding

Hollow Inner mouthpiece B is manufactured by one of the following process

1. Multi-step process: Separately injection mold partial hollow tube followed by bonding these two pieces to create hollow passage way in inner mouth piece.
2. One step injection molding process where partial walls of tube and mouthguard are molded in two cavities of a single mold, followed by rotating cavities where two halves are aligned and second material is injected at intersection, bonding these two pieces and creating hollow structure. Here, the second material is soft material or "Boil and Bite" material, creating customized oral device in a single step process.
3. Water or gas injection molding to achieve hollow air passage way
4. Lost core foam injection molding

Customizations of mouthguard on Inner Piece B (to fit the teeth perfectly) is achieved by processes such as
1. "boil and bite" concept – Mechanical bonding or two shot molding and
2. Micro-cellular foaming injection molding processes.

OR customized device is made by 3D Printing process (plastics or metal) as one piece or A and B separately OR Boil and Bite overmolding on 3D printed hollow device

Final Device Assembly – Snap fit Hollow Housing A and Hollow inner piece B, followed by inserting micro blowers, other items and control module

Fig. 12

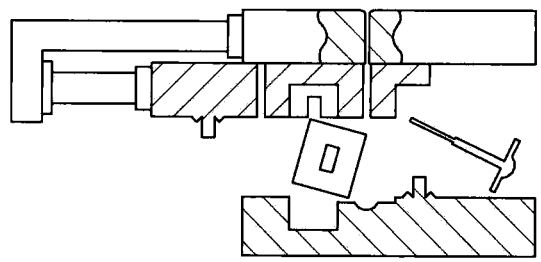
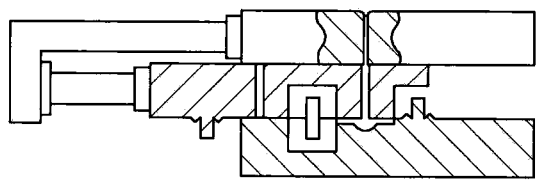
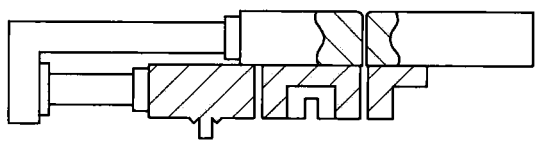
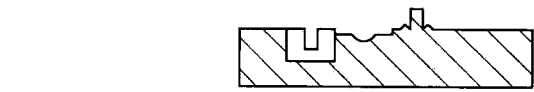
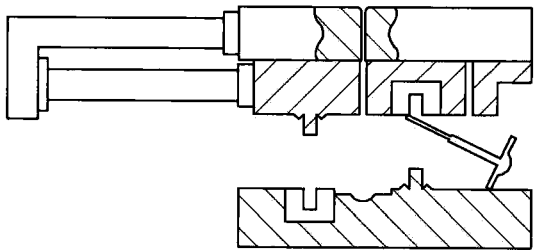
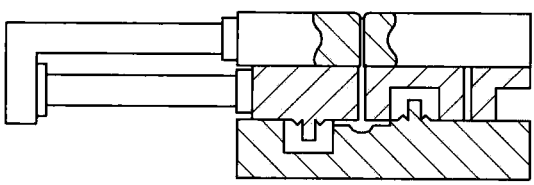
FIG 15

SLEEP APNEA AND ANTI-SNORING SYSTEM

CROSS-REFERENCE TO RELATED APPLICATIONS

This application claims the benefit of U.S. Provisional Application No. 62/269,331, filed on Dec. 18, 2015. The entire disclosure of the above application is incorporated herein by reference.

FIELD

The teachings are directed towards sleep apnea/anti-snoring devices and more particularly to a cordless and tubeless hybrid sleep apnea/anti-snoring devices for reducing and measuring sleep apnea and snoring.

BACKGROUND

Obstructive sleep apnea (OSA) is a Sleep disorder with partial or complete cessation of breathing during one's sleep. This sleep disorder is currently treated by methods such as a surgery, oral appliance therapy, negative pressure to pull soft palate and tongue forward, implantable devices that keep the airway open during sleep by stimulating the hypoglossal nerve, strips for nose for expiratory positive airway pressure, Positive Air Pressure (PAP) therapy or a combination involving several methods. PAP therapies are also employed to treat other medical and respiratory disorders, such as Cheynes-Stokes respiration, congestive heart failure, and stroke. A common PAP device comprises a flow generator (e.g., a blower) that delivers gas via delivery conduit (hollow tube) to an individual interface. It is also known to deliver the PAP as a continuous positive airway pressure (CPAP), a variable airway pressure, such as bi-level pressure (Bi-PAP) that varies with the individual's respiratory cycle or an auto-titrating pressure (APAP) that varies with the monitored condition of the individual. Nasal, oral-nasal and full face masks are common interfaces utilized for delivering PAP to the individual's airway.

These masks can be uncomfortable due to improper fit, tight straps to hold mask in place, skin irritation at points of contact, dryness of throat cause claustrophobia, excessive PAP pressure and are a major factor in individual therapy non-compliance. Also the PAP machines can be noisy. Studies show individual non-compliance for PAP therapy from 29 to over 83%.

Obstructive sleep apnea (OSA) is a Sleep disorder with partial cessation (hypopnea) or complete cessation (apnea) of breathing during one's sleep. This sleep disorder is diagnosed and analyzed by a technician monitored overnight sleep study in a sleep laboratory setting (Polysomnography or PSG) with multiple physiological parameters and more recently by Home Sleep Testing devices with limited parameters.

The federal Center for Medicare and Medicaid Services (CMS) has provided guidance for various types of sleep studies based on number of parameters and whether study is attended by Sleep technician or is unattended. A brief summary of the classification system for sleep studies based on these guidelines is provided below.

Most of the current Home Sleep Testing (HST) devices are worn on chest while current device of invention is only device which is worn in mouth. It is very comfortable, convenient, small in size and provide for more information due to proximity of several sensors to nose and mouth where actual sleep disturbances events should be measured.

Type I HST devices using in attended sleep studies performed in a sleep lab and monitored by a sleep technician with full sleep staging (i.e monitoring the transition through the various sleep stages). Typically, Type I devices include the following channels (parameters): EEG (electroencephalogram), EMG (electromyogram —chin and Limb), EOG (electrooculogram), respiratory airflow (with oronasal flow monitors), respiratory effort (Thorax and Abdomen), oxygen saturation (oximetry), ECG (electrocardiography), snoring sounds, and body position—additional channels for CPAP/Bi PAP levels, CO2, pH, pressure etc.

Type II Home sleep test (HST) devices use a portable monitor, performed without any sleep technician monitoring the study, with at least 7 channels or parameters. Type II devices typically include at the very least the following Parameters: EEG, EOG, ECG/heart rate, EMG, Airflow, Respiratory effort, Oxygen saturation. Type III Home sleep tests (HST) use a portable monitor unattended with a minimum of 4 channels. Type III devices usually include the following parameters: 2 respiratory movement/airflow, 1 ECG/heart rate, 1 oxygen saturation. Type IV Home sleep test (HST) with Type IV portable monitor, unattended with a minimum of 3 channels. Type IV devices must allow parameters that allow direct calculation of an AHI (Apnea Hypopnea Index) or RDI (Respiratory Disturbance Index) as the result of measuring airflow or thoracoabdominal movement. The RDI is defined as the average number of respiratory disturbances.

Alternately devices that record other information to derive AHI or RDI must be approved by CMS through the review of published peer reviewed medical literature. It is very expensive to perform the traditional attended PSG sleep studies in sleep labs (Type I) to diagnose for OSA. Patients have difficulty getting to sleep in a unfamiliar surrounding with various wires connected to their limbs and head and being continuously watched and monitored. This created a need for a simpler and cheaper way to diagnose for OSA and led to the development of portable sleep monitors—Home Sleep Testing machine (HST) complying with the CMS guidelines and offering results comparable to that of PSG in a home setting.

SUMMARY

The teachings relates to oral or nasal or a combination of oral and nasal device for treatment and diagnosis of obstructive sleep apnea and snoring; having microprocessors and sensors, can include the following configurations and all devices are with or without mandibular advancement (MAD): Oral Device having micro-blowers and control module—positive airflow (PAP) device; Oral Device having micro-blowers and control module—auto control positive airflow (Auto PAP) device and proprietary algorithm for auto adjustment of pressure and/or flow rate; Oral/Nasal Device having micro-blowers with positive airflow (PAP or APAP) utilizing nasal passage for air delivery; Oral Device without micro blower and with or without microprocessor, sensors and data acquisition system; and the above oral devices with capability for testing sleep apnea known as HST or OOCST (out of center sleep testing) diagnostic PAP device and capability to treat OSA.

All above configurations according to the teachings within this application can be without mandibular advancement (MAD) and can be provided with upper mouth piece only (i.e. without the lower mouth piece) or with lower mouth piece only (i.e. without the upper mouth piece). All above devices can be customized or non-customized by using casting, 3d printing or boil and bite techniques.

According to the present teachings, an oral sleep apnea treatment device selectively engagable with a patient's lips and teeth is presented. The oral sleep apnea treatment device includes a front hollow housing defining a first through passage, said front hollow housing having an exterior surface configured to engage the patient's lips. A mouthpiece is provided having an exterior surface defining a tooth engaging surface and defining second and third through passages, each defining an aperture disposed adjacent to the adjacent to the retromolar pad members when engaged with the patient's teeth. A pressure and/or air flow generating device in the form of a blower is disposed within the first through passage. The pressure and/or air flow generating device configured to create an airflow through the second and third passage and adjacent the retromolar pad members.

According to another teaching, the device has a battery disposed within the front hollow housing, said battery being electrically coupled to the pressure and/or air flow generating device.

According to another teaching, the afore mentioned device has a controller configured to regulate electrical power supplied to the pressure and/or air flow generating device.

According to another teaching, in the afore mentioned device the front hollow housing is selectively engageable to the mouthpiece.

According to another teaching, the afore mentioned device is formed using one of additive manufacturing, injection molding, and blow molding.

According to another teaching, the afore mentioned device the mouthpiece is injection over-molding with an elastically deformable, low durometer material.

According to another teaching, the afore mentioned device further has first and second members having member defining a u-shape said first and second members defining the defining second and third through passages, and a plurality of flanges disposed between the first and second members and said plurality of flanges engaging a tongue.

According to another teaching, the afore mentioned the mouth piece has first and second u shaped components, the first and second u-shaped members defining the second and third through passages.

According to another teaching, the afore mentioned device further has a control module in the front hollow housing, wherein the control module is coupled to a plurality of sensors, the control module configured to provide a signal to control operation of the pressure and/or air flow generating device.

According to another teaching, the afore mentioned device includes a plurality of sensors which can be one of a pressure sensor, an airflow sensor, temperature sensors, sound sensor, an accelerometer, and a pulse oximeter According to another teaching, the afore mentioned device wherein the control module has a closed loop control system and a wireless communication module.

According to another teaching, the afore mentioned devices further having a mandibular advancement device.

According to another teaching, the afore mentioned device further including a nostril tubes in connection to the front hollow housing to a nasal passage.

According to the present teachings, an home sleep test device is provided which is selectively engagable with a patient's lips and teeth. The home sleep test device includes a front hollow housing defining a first through passage, the front hollow housing having an exterior surface configured to engage the patient's lips. A mouthpiece is provided having an exterior surface defining a tooth engaging surface and defining second and third through passages, each defining an aperture disposed adjacent to the adjacent to the retromolar pad members when engaged with the patient's teeth. A data acquisition system within the first through passage. The data acquisition system is configured to measure an airflow through the second and third passage and adjacent the retomolar pad members.

According to another teaching, the device has a battery disposed within the front hollow housing, said battery being electrically coupled to the controller.

According to another teaching, in the afore mentioned device the front hollow housing is selectively engageable to the mouthpiece.

According to another teaching, the afore mentioned device is formed using one of additive manufacturing, injection molding, and blow molding.

According to another teaching, the afore mentioned device the mouthpiece is injection over-molding with an elastically deformable, low durometer material.

According to another teaching, the afore mentioned device further has first and second members having member defining a u-shape, said first and second members defining the defining second and third through passages, and a plurality of flanges disposed between the first and second members and said plurality of flanges engaging a tongue.

According to another teaching, the afore mentioned the mouth piece has first and second u shaped components, the first and second u-shaped members defining the second and third through passages.

According to another teaching, the afore mentioned device further has a control module in the front hollow housing, wherein the control module is coupled to a plurality of sensors, the control module configured to provide a signal to control operation of the pressure and/or air flow generating device.

According to another teaching, the afore mentioned device includes a plurality of sensors which can be one of a pressure sensor, an airflow sensor, temperature sensors, sound sensor, an accelerometer, and a pulse oximeter.

According to another teaching, the afore mentioned device wherein the control module has a closed loop control system and a wireless communication module.

According to another teaching, the afore mentioned devices further having a selectively adjustable mandibular advancement device The teachings additionally relate to device designs and functioning of device manufacturing methods, and materials for single piece, micro, tubeless, cordless, anti-snoring (AS)/sleep apnea treatment (SA) devices where airflow from the front of the mouth is directed from the device to the back of the mouth, bypassing the soft tissues, palates, tongue etc. This flow can be directly to the oropharynx or laryngopharynx area, with or without use of micro-blowers (and with or without microprocessor/sensors in both cases). The device can be attached to the upper arch (teeth) or the lower arch (teeth) or to both arches. The design of the device allows for simultaneous nose and mouth breathing.

The device can be non-customized or customized for the individual. Air-flow is directed to the oropharynx area (throat area) from the mouth opening (lips area) using a front hollow housing and hollow tubes or other hollow shapes passageways attached to inner mouthguard bypassing soft tissues. In case of standard CPAP configuration, air flow at a predetermined air flow rate and pressure is supplied. In case of an Auto PAP device, the pressure and airflow is continuously adjusted as per need using micro fan(s), sensors and microprocessor with firmware (algorithm). In addition to an auto continuous positive air pressure (Auto CPAP) or non-auto continuous positive air pressure (CPAP) controlled mechanism, the oral device can also bring lower jaw forward (mandibular advancement device—MAD), increasing air passage, further mitigating OSA and snoring.

This hybrid device is referred to herein as a single piece Oral CPAP with MAD device. In all above concepts, the device has the capability to record data within the system using a micro-SD card or to transfer data wirelessly to mobile devices or to cloud using Bluetooth to permit live monitoring of the medical condition of the individual and treatment compliance. The device can record data (air flow rate, respiratory efforts, oxygen saturation, pressure, temperature, snoring pattern, and position during sleep) which can be used to determine sleep parameters such as AHI (Apnea/Hypopnea) index, SpO2, snoring level, breathing variation etc., using proprietary algorithm.

The afore mentioned devices according to the present teachings can be controlled by preprogrammed algorithms or by wirelessly updating with mobile device of parameters such as pressure, flow rate, mode of operation etc.

The afore mentioned devices according to the present teachings can also utilize active noise cancellation techniques and passive methods such as specific sound insulating/absorbing materials to reduce the noise from the operation of the device.

The afore mentioned devices according to the present teachings can also incorporate features for tongue movement control such as preventing it from falling to the back of mouth and creating obstruction to the air way passage.

The afore mentioned devices according to the present teachings can be without micro blowers (or may be also without hollow tubes) can also be used as diagnostic sleep apnea device such as Home Sleep Study (HST) device. The sensors to measure air flow directly or differential pressure to measure the airflow while breathing (air flow limitation to calculate AHI index); a pulse oximeter to measure SpO2, heart rate and temperature; a position sensor (tilt sensor) to indicate position of body while at sleep, Sound sensor to measure breathing variation and snoring; miniature video camera mounted on the mouthguard to take pictures of inside of mouth during sleep and a processing unit to capture and analyze these parameters to provide a comprehensive sleep study report for a type 3 and other types HST device. These parameters are captured on a memory card built into the unit or wirelessly transferred using Bluetooth, wifi, cloud or other similar technologies.

The afore mentioned devices according to the present teachings can be formed of two pieces: a front hollow housing (in which micro fan(s), sensors, microprocessors etc. are inserted after manufacturing) and an inner mouth piece with hollow air passage way. These pieces have snap fit and easy unsnap fit features.

The afore mentioned devices according to the present teachings can be formed of a plurality of processes. For example, the front hollow housing with is made by injection molding, while hollow passage way for inner mouthpiece can be achieved by. Multi-step process: separately injection mold partial hollow tube followed by bonding these two pieces to create hollow passage way in inner mouth piece; one step injection molding process with multi cavities and rotating tool; water or gas injection molding to achieve hollow air passage way; and lost core foam injection molding.

The afore mentioned devices according to the present teachings can be both non-customized and customized devices are manufactured by similar processes as described above except for customizations (to fit the teeth perfectly) is achieved by processes such as 3D printing (hard or hard/soft materials), "boil and bite" concept and micro-cellular foaming injection molding processes.

The afore mentioned devices according to the present teachings can bring airflow from the front of the mouth to back of the throat (pharynx area) and can be combined with mandibular advancement (bringing the lower jaw forward) to further assist in eliminating or reducing snoring and sleep apnea, referred to herein as PAP-MAD without microblower (with or without microprocessor and sensors) or PAP-MAD with micro-blower(s) and microprocessor and sensors or Auto-CPAP/MAD with micro-blower(s) having sensors/microprocessor and closed loop control system and algorithm to have comfortable pressure/air flow change during sleep.

According to another teaching, the afore mentioned structures can be used for oral or nasal or a combination of oral and nasal device as Home Sleep Testing (HST) device for the diagnosis of obstructive sleep apnea (OSA) and snoring. The HST can include having microprocessors and sensors.

The HST unit for standard OSA testing without mandibular advancement (MAD) can be provided with upper mouth piece only (i.e. without the lower mouth piece) or with lower mouth piece only (i.e. without the upper mouth piece).

According to an alternate teaching, the HST unit can include mandibular advancement (MAD) to validate specific mandibular advancement setting and treatment of sleep apnea with or without innovative oral CPAP sleep apnea device or current CPAP device.

According to an alternate teaching, the HST unit can be used in conjunction with CPAP for determining the efficacy of a pressure setting.

According to an alternate teaching, the HST unit can device as sleep apnea diagnostic as well as treatment device: In addition to device performing as diagnostic tool (as Home Sleep Testing (HST) or Out of center Sleep Testing (OOCST) for detecting OSA, the same device can also be used as sleep apnea treatment and/or anti-snoring device.

According to an alternate teaching, the HST unit can be fitted with a mix of sensors to measure air flow; SpO2 (oxygen saturation in blood), heart rate (beats/min) and respiratory effort. These parameters would be sufficient to perform a sleep study conforming to the guidelines by CMS or AASM for a Type III or Type iV study. Additional sensors can be included to measure temperature; body positions while at sleep, Sound (breathing) variation and snoring, Single channel ECG (heart), EEG for brain activity etc.

Actual sleep time is not measured by current HST devices while in one embodiment the device can have built-in sensors or wirelessly communicating sensors like heart rate, breathing monitoring, position sensor for body movement during sleep, temperature along with proprietary algorithm helps in measuring actual (true) sleep time which is very important for accurate (true) AHI number, a measure of severity of sleep apnea.

In one embodiment, the device would be fitted with a differential pressure sensor to measure airflow and pressure (or alternately with a PVDF calibrated strip), a novel pulse ox sensor from lips for oxygen saturation and heart rate (alternately could be a standard pulse oximeter with Bluetooth capability), and a photophlethysmographic (PPG) sensor to measure respiratory effort (alternately could be a standard RIP belt to acquire the same parameter). All these parameters would be continuously acquired and stored on a memory SD card built into the unit (device) or wirelessly transferred using Bluetooth, wi-fi, cloud or other similar technologies to a mobile device or to cloud based server. This data can then be analyzed by automated computer algorithms for episodes of breathing irregularities while sleeping—such as apneaic or hypopneaic events and summarized to provide AHI/RDI information. The RDI is defined as the average number of respiratory disturbances. The device can be controlled wirelessly using mobile devices.

In another embodiment, the device can be enhanced by addition of sound sensor to measure breathing patterns and snoring variation, thermistor for temperature of air flow and breathing pattern, miniature video camera mounted on the mouthguard to take pictures of inside of mouth during sleep and a processing unit to capture and analyze these parameters to provide a far more comprehensive sleep study report compared to the Type III or Type IV HST devices.

Both of above embodiments can be adapted to validate Mandibular Adjustment (MAD) setting by providing oral component with mandibular adjustments (lower jaw advancement) in specific fine increments.

Also the device of present invention can be concurrently used with CPAP and validate efficacy of pressure setting for the CPAP treatment.

DRAWINGS

Figure 1A:
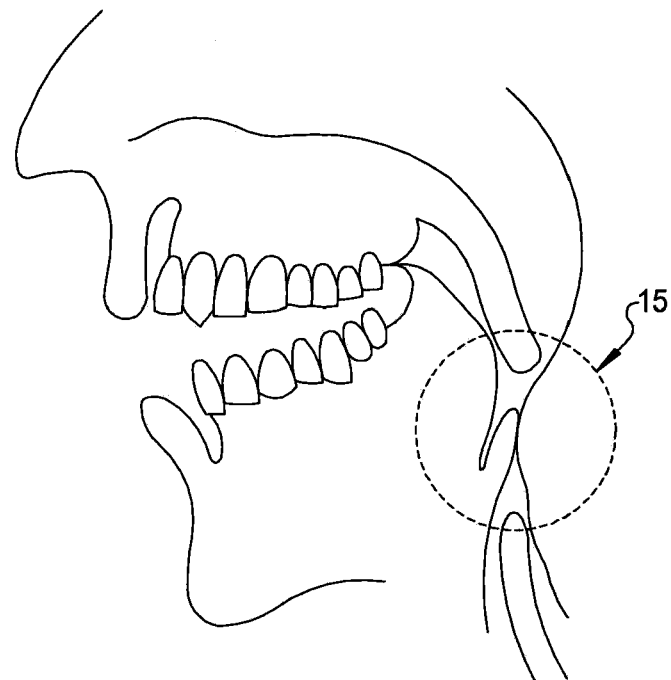
FIGS. 1A to 1I depict various embodiments of a sleep apnea treatment or anti-snoring device attached to upper arch with hollow front housing and hollow side tubes (with or without microprocessor/sensors attached to front hollow housing) to bring air at the end of the throat (pharynx) area according to the present teachings.
Figure 1B:
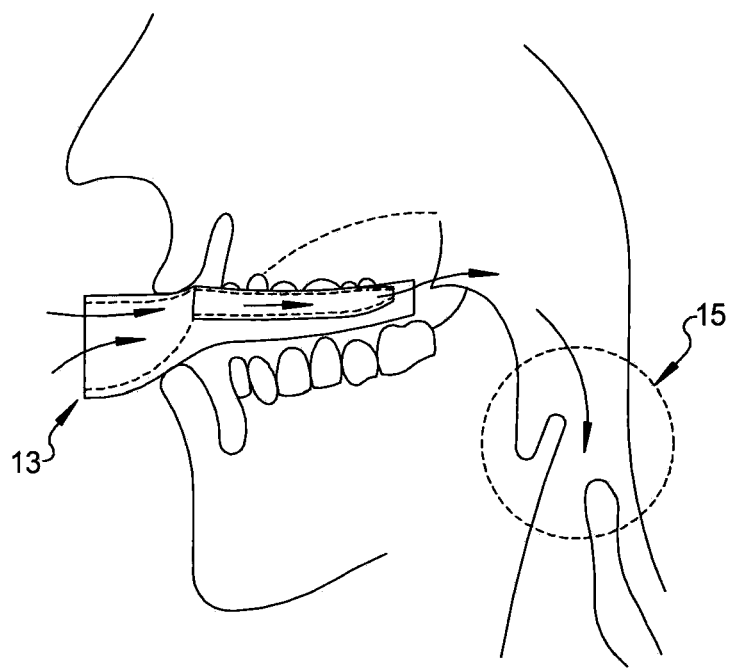
Figure 1C:
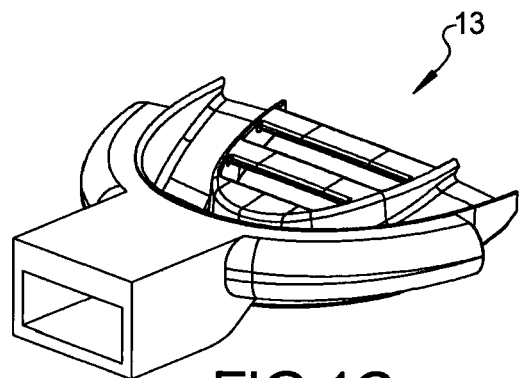
Figure 1D:
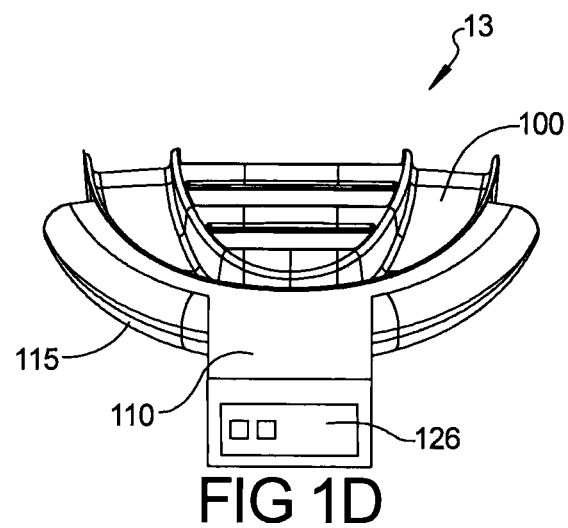
Figure 1E:
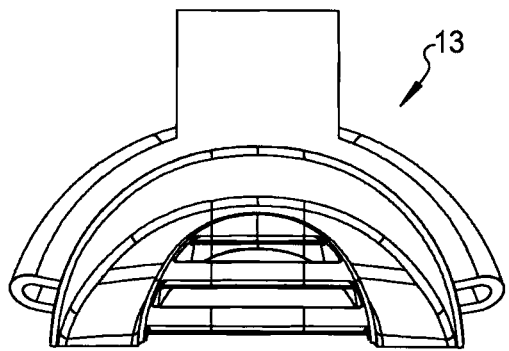
Figure 1F:
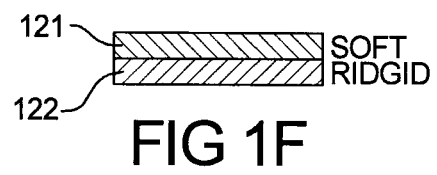
Figure 1G:
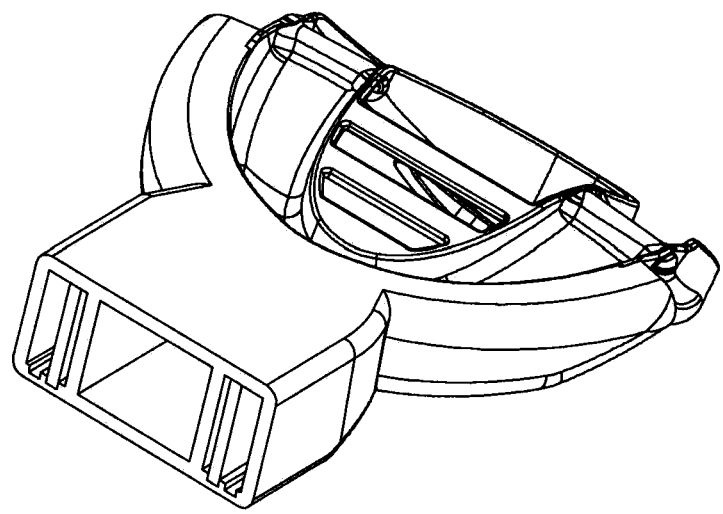
Figure 1H:
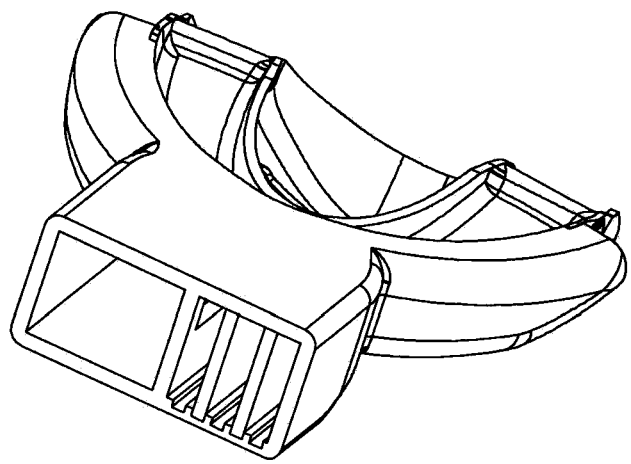
Figure 1I:
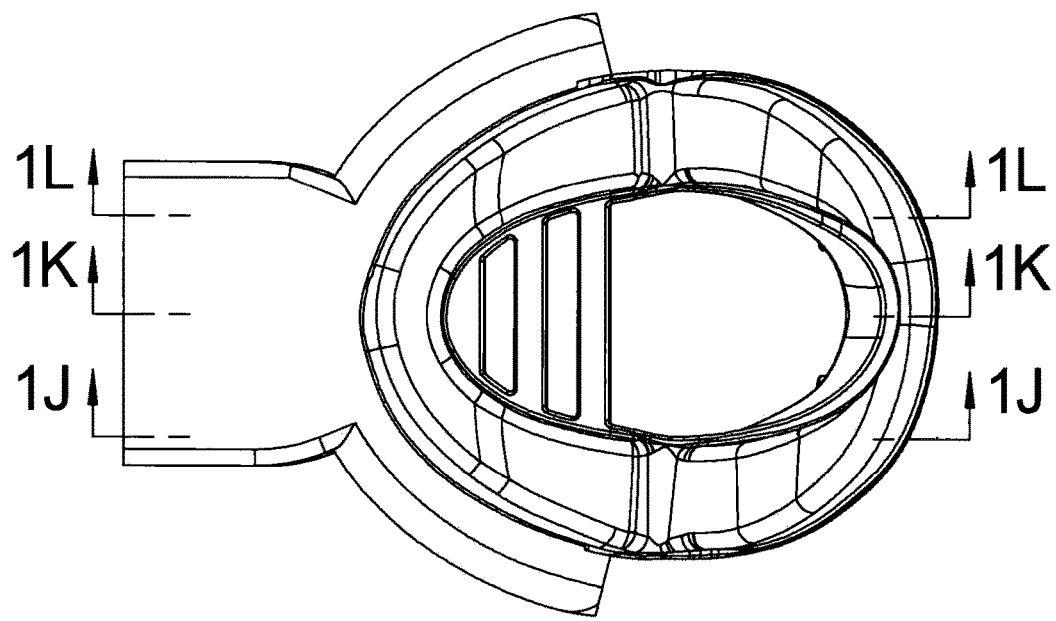
Figure 1J:
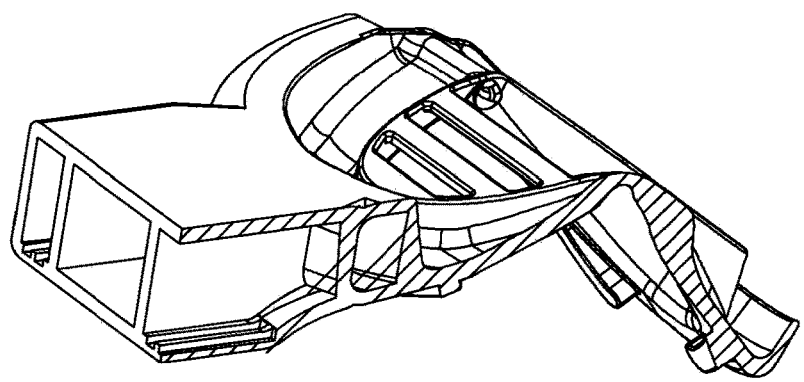
FIG. 1J depicts different cross sections of device—from front of the housing to end of inner piece (oropharynx area) according to the present teachings.
Figure 1K:
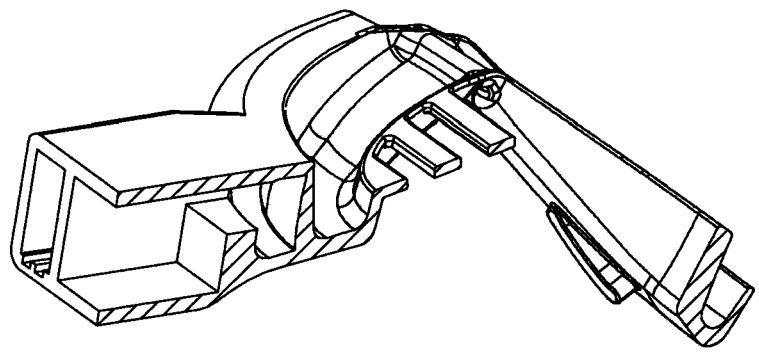
FIG. 1K shows further cross section at the center of device as per FIG. 1I cross section.
Figure 1L:
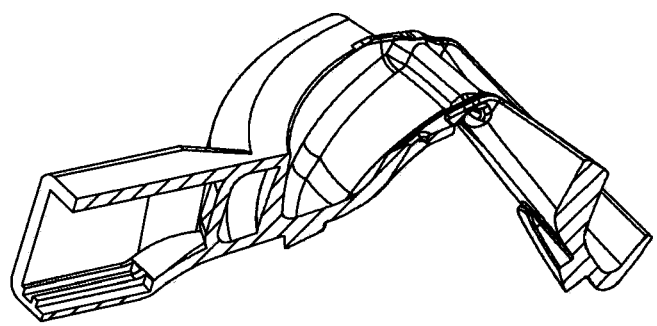
FIG. 1L shows further cross section at the center of device as per FIG. 1I cross section
Figure 1M:
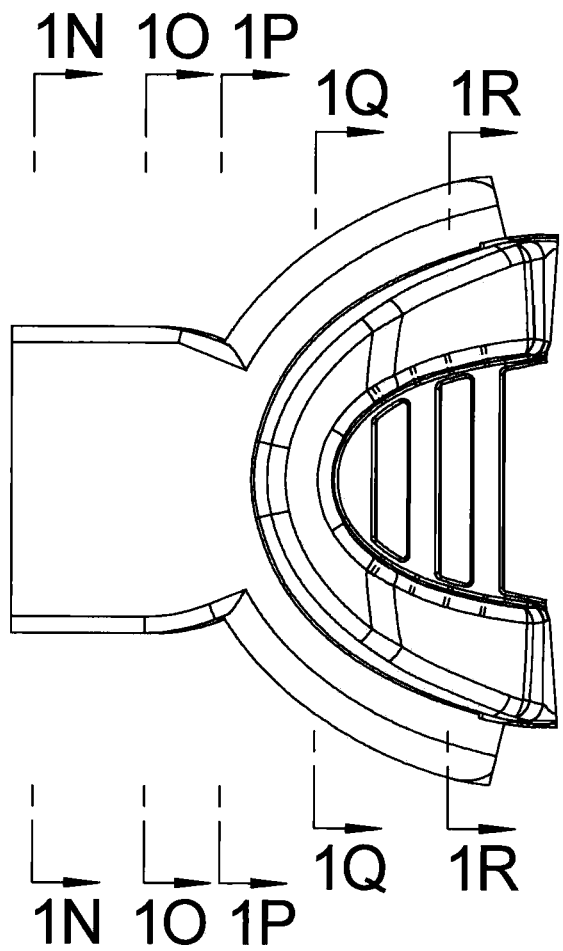
FIG. 1M shows the device with cross section areas to be taken for further figures and FIG. 1N depict one cross section of device as per FIG. 1M.
Figure 1N:
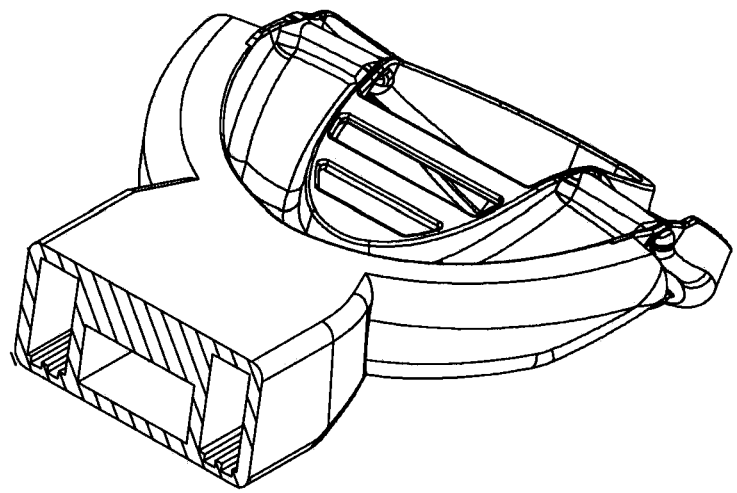
Figure 1O:
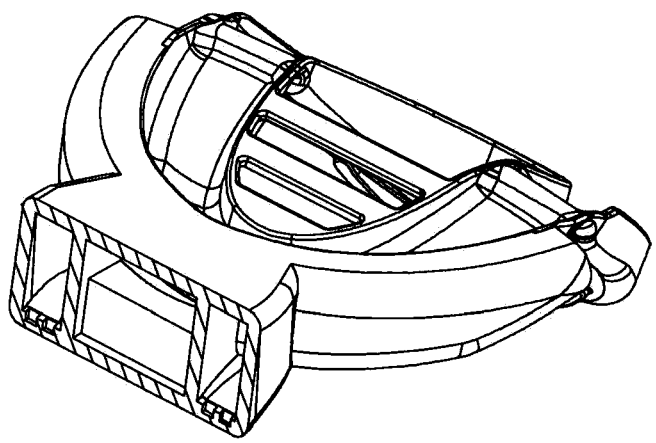
FIG. 1O shows the next cross section as per FIG. 1M.
Figure 1P:
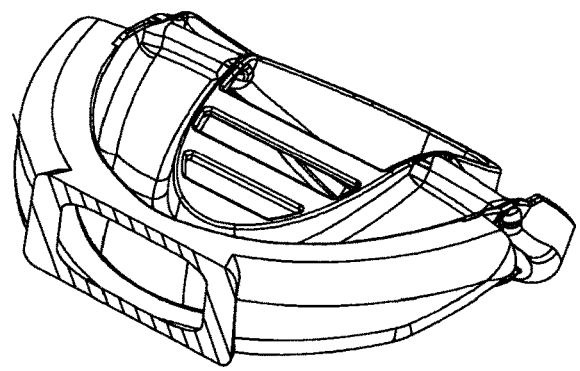
FIG. 1P depicts the next cross section as per Figure.
Figure 1Q:
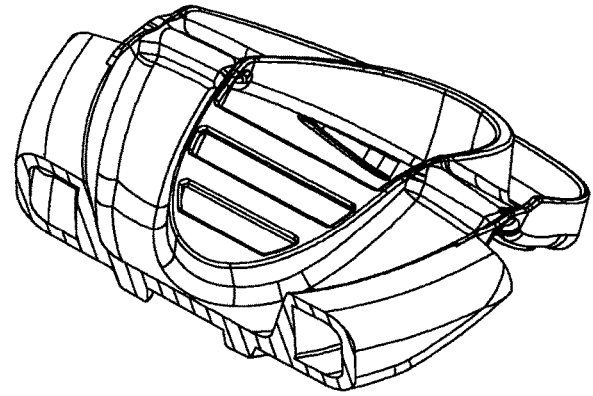
FIGS. 1S-1Y represent various views of the device shown in 1O.
Figure 1R:
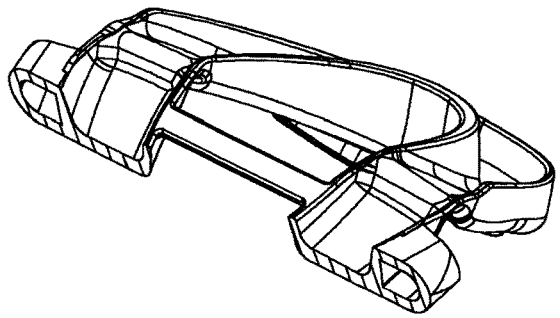
Figure 1S:
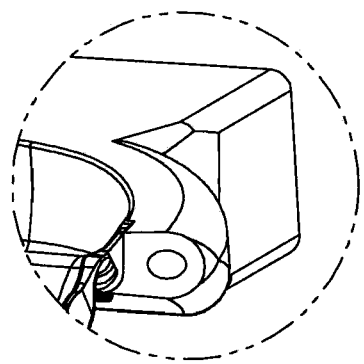
Figure 1T:
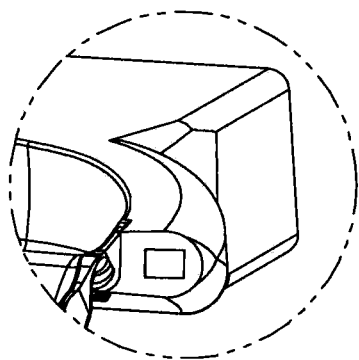
Figure 1U:
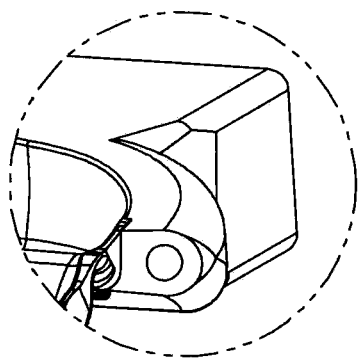
Figure 1V:
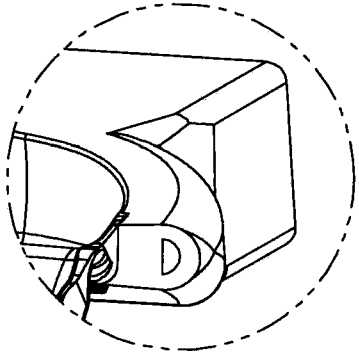
Figure 1W:
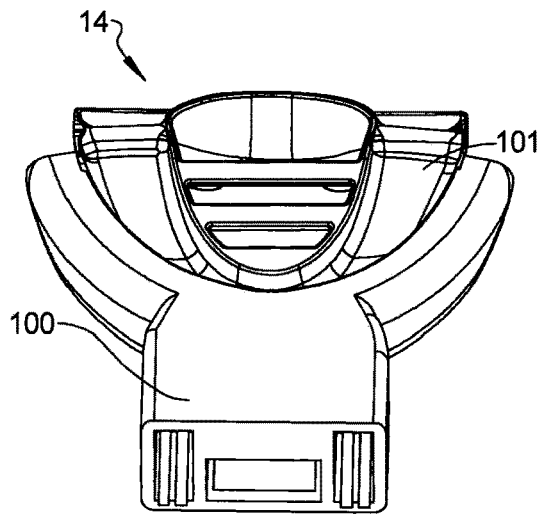
Figure 1X:
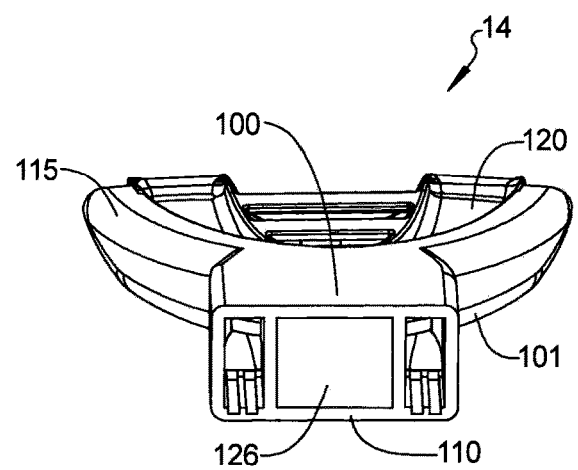
Figure 1Y:
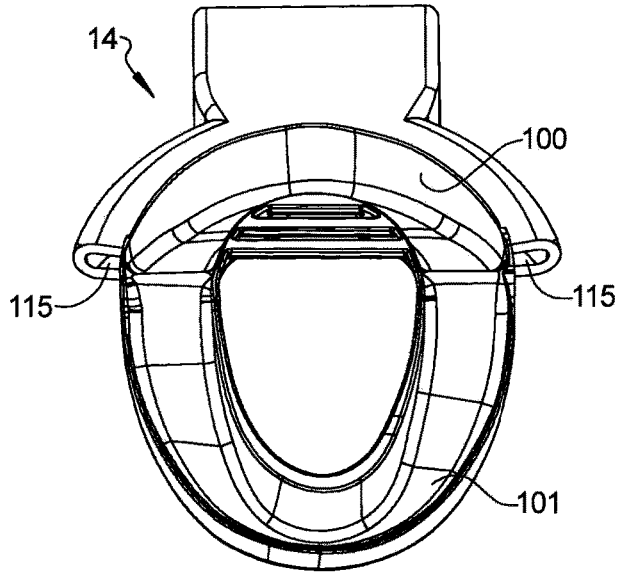
Figure 2A:
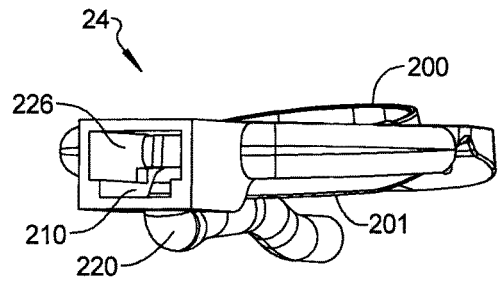
Figure 2B:
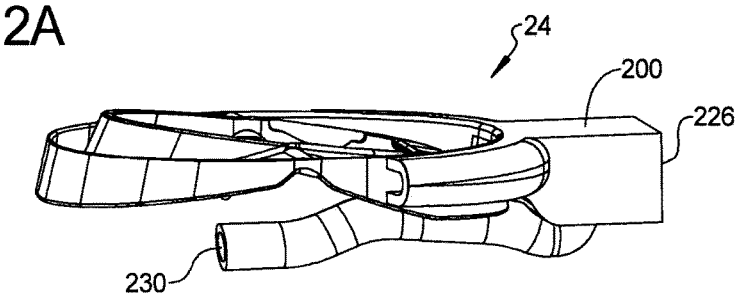
Figure 2C:
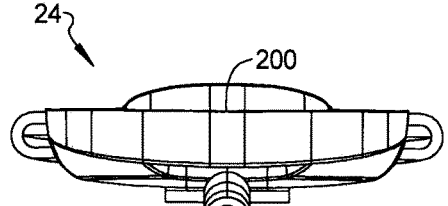
Figure 2D:
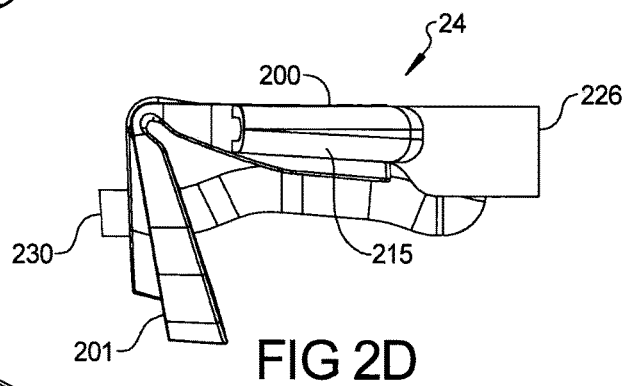

FIGS. 1Q and 1R further depict the cross sections to the present teachings;

FIG. 2A to 2C depict a sleep apnea or anti-snoring device with both upper and lower arches, where the upper arch comprises a curved center hollow passageway designs from front of mouth other than hollow tube to keep the tongue down while delivering airflow directly to the oropharynx/throat area according to the present teachings;

FIG. 2D shows hollow tube or hollow passageway design according to FIG. 2 having a lower portion rotated with respect to an upper portion.

Figure 2E:
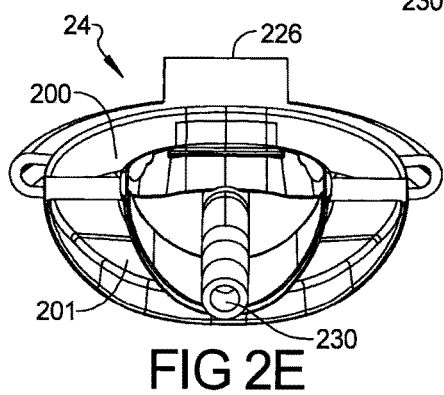
Figure 3A:
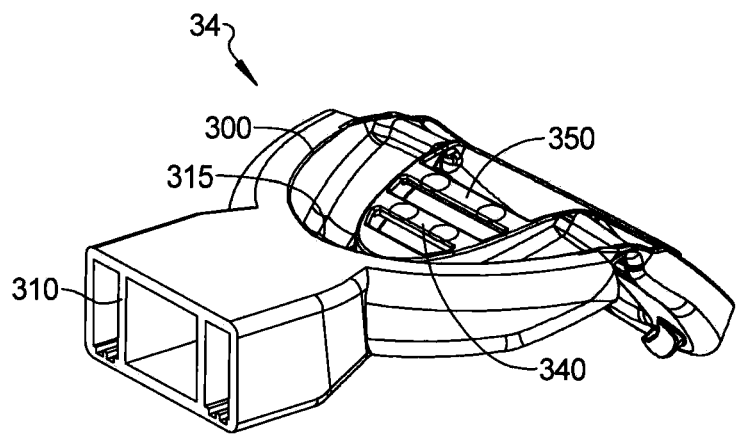
Figure 3B:
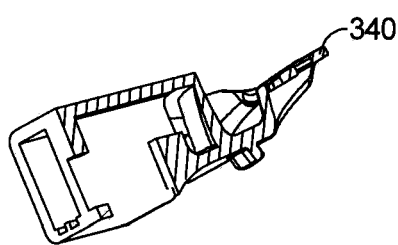
Figure 6A:
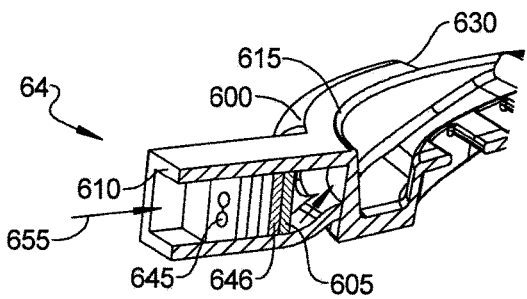
Figure 6B:
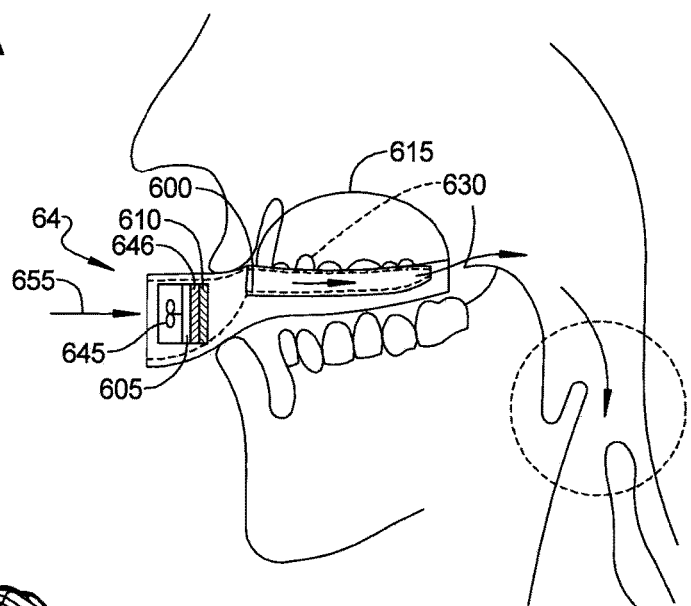
Figure 6C:
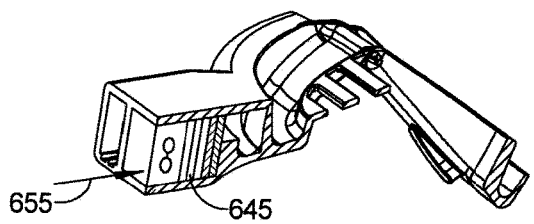
Figure 6D:
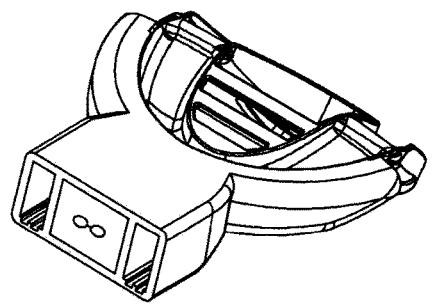
Figure 7A:
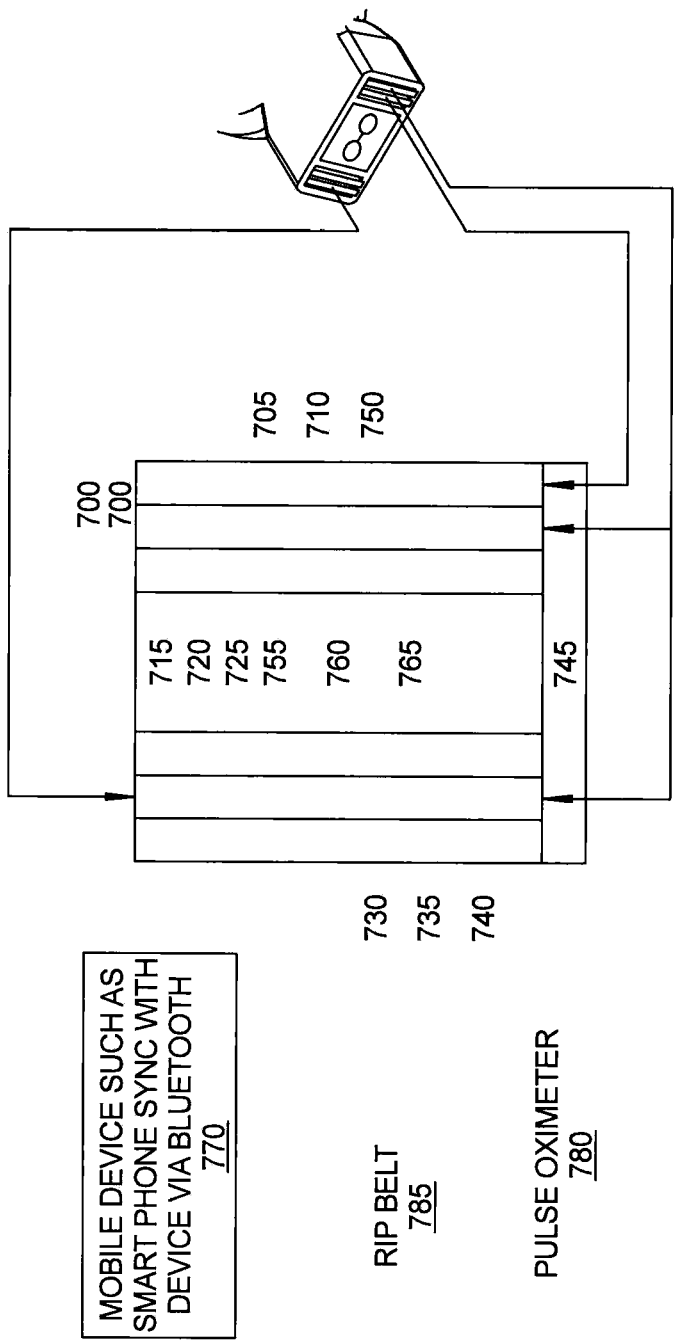
Figure 7B:
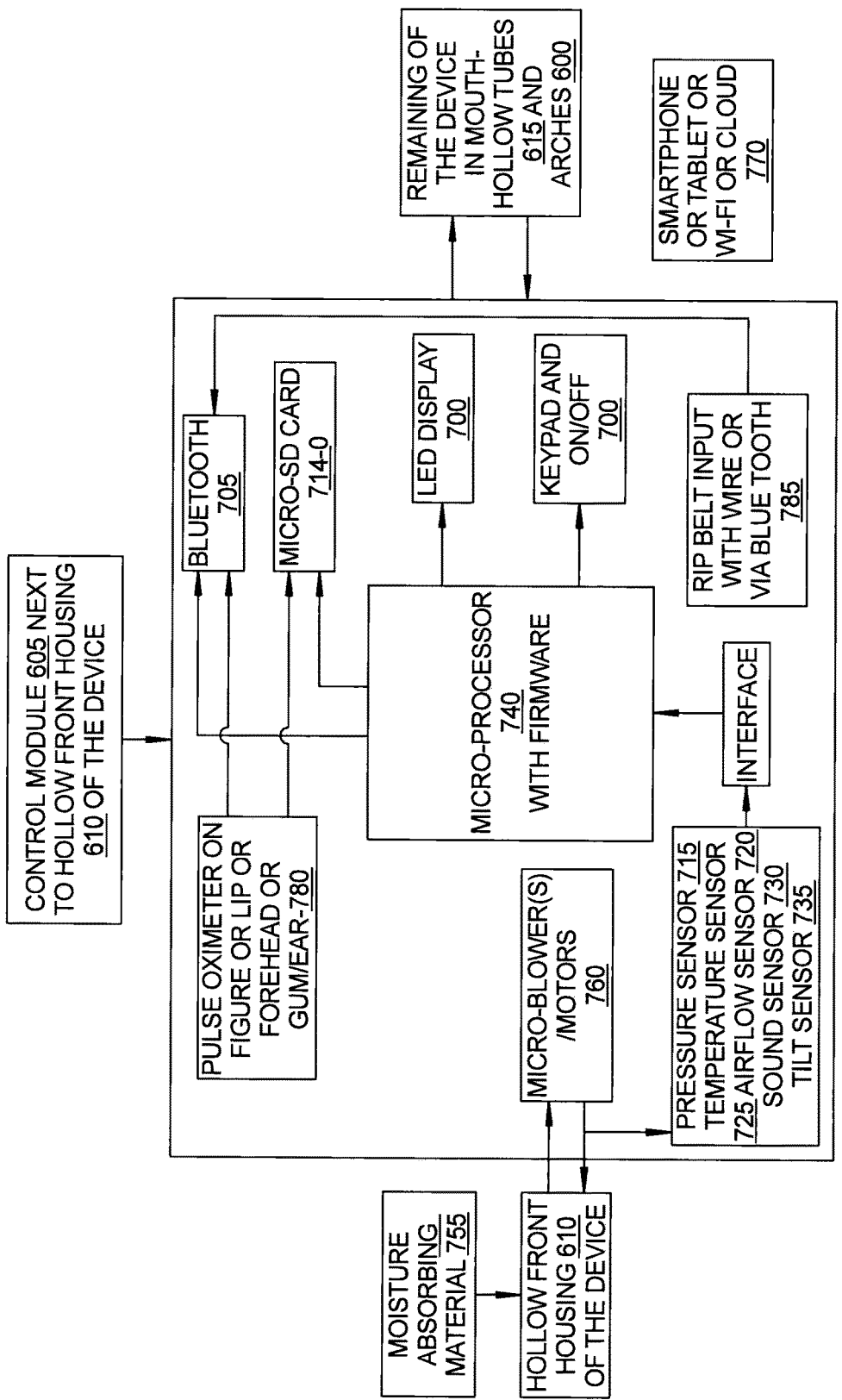
Figure 8A:
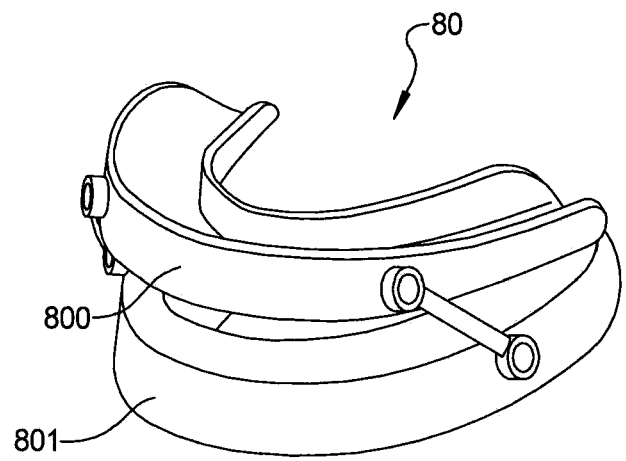
Figure 8B:
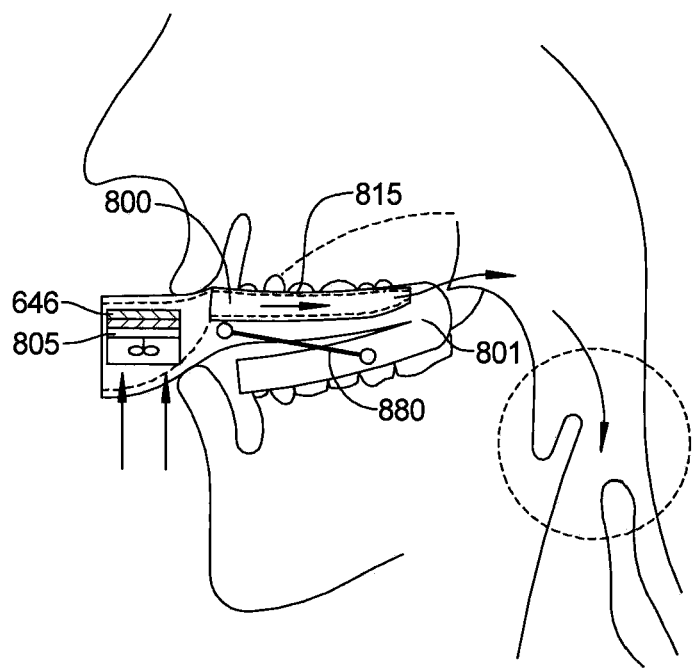
Figure 9:
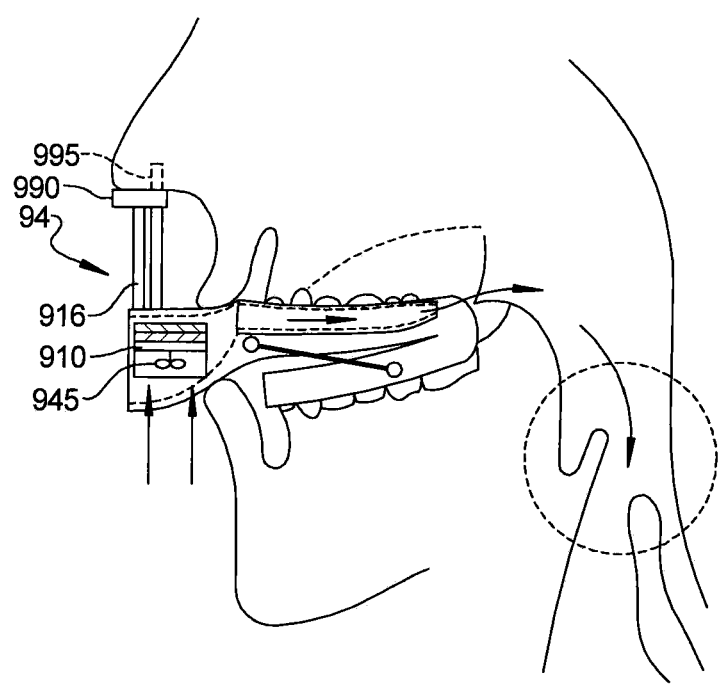
Figure 10:
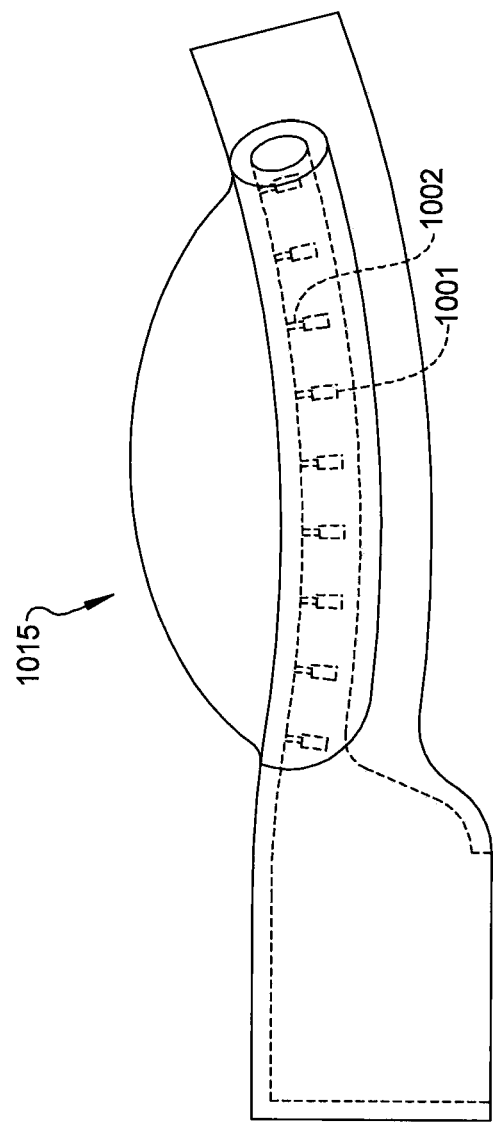
Figure 16:
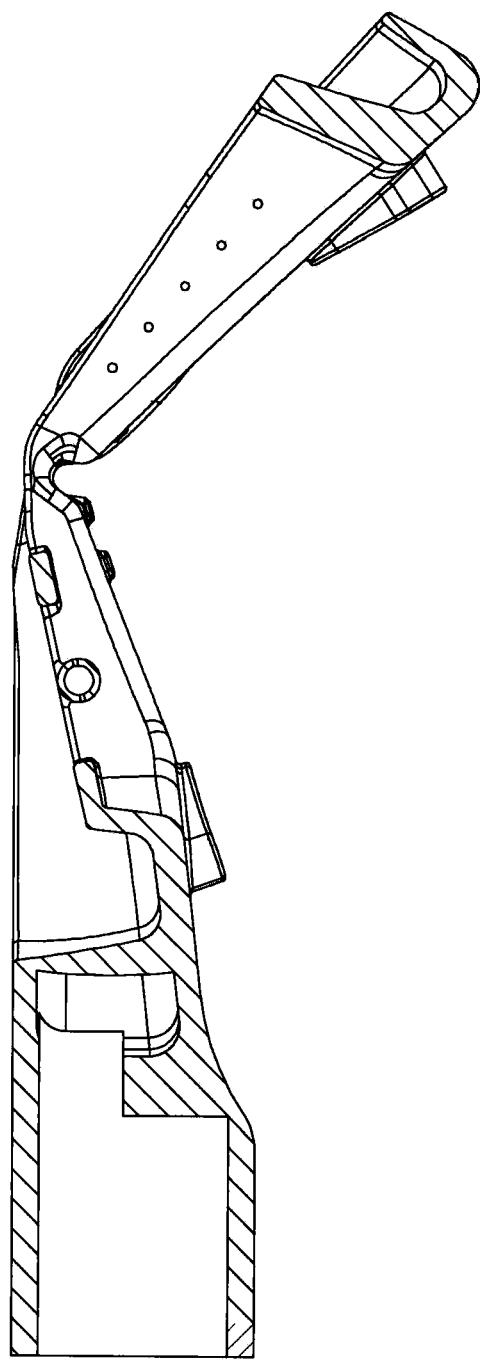
Figure 17:
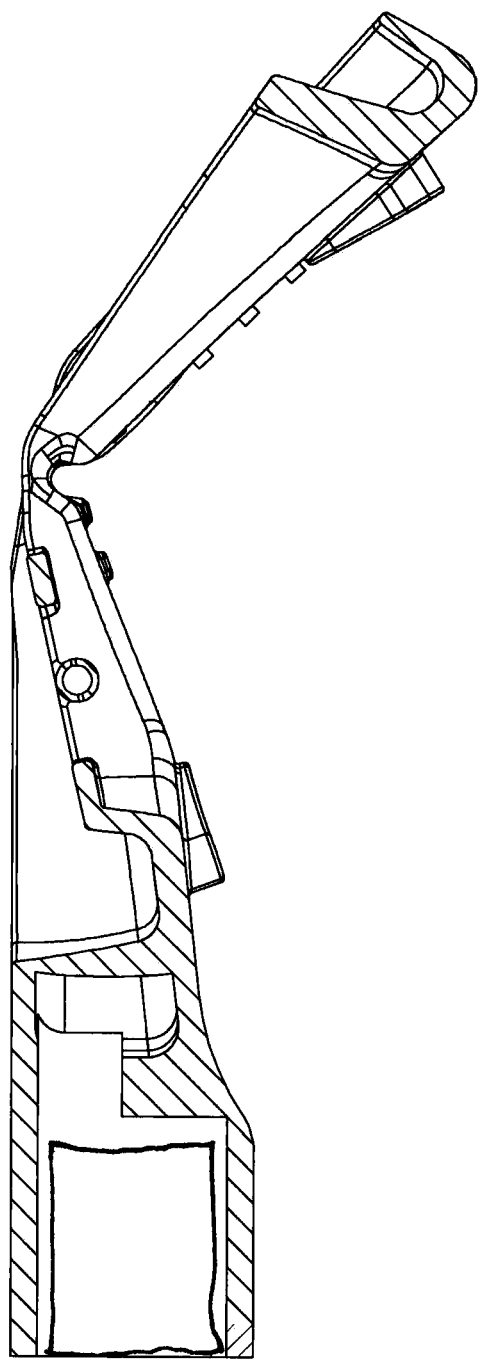

FIG. 2E shows an end view of the hollow tube or hollow passage way design shown in FIG. 2D;

FIGS. 3A and 3B depict a sleep apnea or anti-snoring device with different designs of strips with two sided adhesive buttons or tapes to keep the individual's tongue forward while still allowing tongue side to side movement according to the present teachings;

FIGS. 4A-4E depict conventional CPAP single piece oral sleep apnea treatment device with micro-blower(s) for continuous positive airflow with microprocessors and sensors according to the present teachings;

FIGS. 5A-5D depict a variety of suitable micro-blowers for use with the teachings;

FIGS. 6A and 6B depict an Auto CPAP (APAP) device with a miniature control module inserted in hollow housing having micro-blower(s) and sensors and microprocessor (micro-chip) etc.;

FIGS. 6C and 6D depict micro fan(s) is mounted vertical, blowing the air straight into housing and hollow tubes. FIG. 6D Show that micro fan(s) can be mounted horizontal and control module can be mounted vertically to each according to the present teachings;

FIG. 7A depict an CPAP or Auto-CPAP (APAP) control module comprising various items inserted in the housing of the device;

FIG. 7B depicts a schematic of the data flow and control module according to one embodiment of the teachings;

FIG. 8A depicts current mandibular advancement device (MAD) and FIG. 8B depicts a combination micro, tubeless, maskless, single piece Oral CPAP device with mandibular advancement capability (Hybrid PAP-MA Oral Device or Hybrid APAP-MA Oral Device);

FIG. 9 depicts one embodiment of a nasal/oral device with or without the MAD CPAP Device;

FIG. 10 depicts thin plastic membrane which depresses the upper arch of mouthguard (at the end, throat area) which expands and stays expanded during air flow from micro blower, stopping soft palates to collapse, allowing more open airway passage;

FIG. 11 depicts exploded view of separate pieces of device to be manufactured;

FIG. 12 depicts various flows schemes for manufacturing methods for a Customized, single piece, micro oral PAP or APAP device;

FIGS. 13A-13D depict a customized, single piece, micro oral PAP device made by a "Boil and Bite" manufacturing process;

FIGS. 14A-14D depict a customized, single piece, micro oral PAP device manufactured by "Bite only" micro-cellular foaming injection molding;

FIG. 15 depicts a single step manufacturing method for hollow device by injecting material in two cavities, cavities rotation, followed by injecting plastic at intersection of two halves, creating hollow part;

FIG. 16 depicts micro-holes in the hollow tube (or hollow passage way), blowing air at very low flow rate, but stimulating the tongue to stay forward original position (does not allow to fall back) during sleep. These micro-holes can be near the tongue (lingual area) and/or at the end of throat area (oropharynx area); and FIG. 17 depicts special microchip embedded into mouthguard for nerve stimulation hand a plurality of metal stimulators. It's designed to be in close proximity to the nerves of the tongue muscle. This reduces the tongue falling back during sleep, allowing more open airway passage.

DETAILED DESCRIPTION

The teachings relates to device designs, working function of device, and manufacturing methods for single piece, micro, tubeless, cordless, anti-snoring (AS)/sleep apnea treatment (SA) devices where airflow from the front of the mouth is directed from the device to the back of the mouth, bypassing the soft tissues, palates, tongue etc., directly to the oropharynx or laryngopharynx area, with or without use of micro-blowers. If micro-blowers are not used, the device can have micro-sensors and microprocessors attached to front hollow housing. The sensors can be insert molded in the inner piece of the device. The device can be attached to the upper arch (teeth) or the lower arch (teeth) or to both arches. The design of the device allows for simultaneous nose breathing. The device can be Non-customized or customized for the individual. Air-flow is directed to the oropharynx area (throat area) from the mouth opening (lips area) using a front hollow housing and hollow tubes (or different hollow passage ways designs) bypassing soft tissues. In case of an Auto PAP device, the desired pressure and airflow is achieved (automatically adjusted continuously during sleep) using micro fan(s), sensors and microprocessor having closed loop feedback control system and proprietary algorithm using a compact control module inserted inside the front hollow housing of the oral or oral/nasal device. Sensors with low energy battery can also be attached to mouthguard during injection molding process for compliance and few data acquisition purposes. The device has the capability to record data within the system using a micro-SD card or to transfer data wirelessly using Bluetooth or cloud to permit live monitoring of the medical condition of the individual and treatment compliance.

In addition to an auto continuous positive air pressure (Auto CPAP) or non-auto continuous positive air pressure (conventional CPAP) controlled mechanism, the oral device can also bring lower jaw forward (mandibular advancement device—MAD) reducing further occurrence of the sleep apnea and snoring significantly, referred to herein as: A. PAP-MAD without micro-blower but with micro sensors and microprocessor or B. CPAP-MAD with micro-blower(s) more micro-sensors and microprocessor or C. Auto-CPAP/MAD with micro-blower(s) having sensors and closed loop control system and proprietary algorithm to have comfortable (auto-adjustable) pressure/air flow during sleep The device can also be modified to use as a diagnostic sleep apnea device with additional sensors. The device can be controlled wirelessly to set parameters such as pressure, flow rate etc., by any wired or wireless device such as a smart phone, smart notebook etc., using Bluetooth type or other wireless technologies.

The teachings relates to oral or nasal or a combination of oral and nasal device for treatment and diagnosis of obstructive sleep apnea and snoring; having microprocessors and sensors, comprising of following configurations and all devices are with or without mandibular advancement (MAD):

1. Oral Device having micro-blowers and control module—positive airflow (PAP) device
2. Oral Device having micro-blowers and control module—auto control positive airflow (APAP) device and proprietary algorithm for auto adjustment of pressure and/or flow rate
3. Oral/Nasal Device having micro-blowers with positive airflow (PAP or APAP) utilizing nasal passage for air delivery
4. Oral Device without micro blower and with or without microprocessor, sensors and data acquisition system
5. Above oral devices with capability for testing sleep apnea known as HST or OOCST (out of center sleep testing) diagnostic PAP device and capability to treat OSA All above configurations without mandibular advancement (MAD) can be provided with upper mouth piece only (i.e. without the lower mouth piece) or with lower mouth piece only (i.e. without the upper mouth piece). The Non-customized device or customized devices (to fit individual's teeth) are supplied in different sizes such as small, medium and large. Both non-customized and customized devices consist of two pieces A and B as shown below: A. front hollow housing (in which micro fan(s), sensors, microprocessors etc. are inserted after manufacturing) and B. inner mouth piece with hollow air passage way.

Front housing has snap/un-snap fit concept where front hollow housing section is easily snap-fitted with inner mouth piece and also can be easily un-snapped (removed from inner mouth piece). Below are manufacturing methods: A. Front hollow housing with is made by injection molding. To prevent air leakage between hollow housing and inner mouth piece, an elastomeric ring is mounted on front housing or elastomeric ring is molded in one step process as two shot injection molding. B. For inner mouthpiece, the following manufacturing methods are used to achieve predetermined hollow passage ways. The inner mouth piece is divided into two portion: 1. Partial hollow tube and 2. Mouthguard (upper or lower arch) 1. Multi-step process: 1. Separately injection mold partial hollow tube and mouthguard (or two shot molding of mouthguard where it can be soft/hard material or "boil bite" soft material with hard material) followed by bonding of partial hollow tube and mouthguard to create hollow passage way in inner mouth piece. The bonding can be mechanical, vibration welding, laser welding or adhesively bonding; 2. One step injection molding process where partial walls of tube and mouthguard are molded in two cavities of a single mold, followed by rotating cavities where two halves are aligned and second material is injected at intersection, bonding these two pieces and creating hollow structure. Here, the second material is soft material or "Boil and Bite" material, creating customized oral device in a single step process; 3. Water or gas injection molding to achieve hollow air passage way; and 4. Lost core foam injection molding Both non-customized and customized devices are manufactured to fit the individual's teeth (upper arch, lower arch or both). The customized device provides better fit and more comfort. The customized device is also supplied in 3 different sizes such as small, medium and large based on internal teeth arch sizes of different individuals.

There are different manufacturing methods for customized devices such as: 3D Printing of Device—This is accomplished by scanning of the teeth or creating an impression of teeth, creating a CAD file of teeth for 3D printing of the device, followed by 3D printing of hard or hard/soft device in a single step. Here, hollow sections such as tubes and hollow housings are manufactured in a single step, due to design freedom of 3D printing process. "Boil and Bite" concepts such as: a) Over-molding of "Boil and Bite" material on 3D printed part (also known as insert molding): This is accomplished by injection molding of soft "Boil and Bite" on hard 3D printed hollow device (part) as an "insert" in injection molding tool. b) Over-Molding of "Boil and Bite" material on previously hollow Injection molded device (part): Injection molding of soft "Boil and Bite" material on previously injection molded hollow device as "an Inert" (here, hollow structure for housing and tubes/hollow air passage way can be manufactured by several methods described above. c) micro-cellular foaming injection molding process where micro-cellular foam material is injected on top of mouthguard.

The device can be single piece construction, if the device does not contain any sensors/microprocessor or sensors/microprocessor and battery are completely sealed, then no need to have snap-fit feature. This single piece construction can be achieved by bonding of two separate injection molded halves at pre-determined line (or separately injection molding hosing with partial tube and mouthguard) followed by bonding these two pieces to create hollow structure or by water injection molding or by lost core foam injection molding.

In all cases, it is recommended to replace mouth piece from front housing or replace "boil and bite" portion of mouth piece once it wears out in order to protect the teeth, keeping correct teeth alignment and not creating TMJ. The front hollow housing with or without microprocessor and sensors can be reused.

For both Non-customized and customized devices, they can be used without micro-blower where air flow is directed from the front to oropharynx area due to hollow tubes or hollow passage ways. Here, the device can have microprocessor and key sensors to provide feedback on sleep quality and AHI index as well as compliance.

For both Non-customized and customized devices a micro-blower or multiple micro-blowers can be inserted into the front hollow housing of the device. The micro-blower continuously blows air into hollow internal airflow passages attached to the mouth guard, thus working as a conventional CPAP machine, but without any external tubes or wires or cords attached.

For device described above, the device can also be fitted with a control module having microprocessor and sensors for pressure, airflow rate, temperature, pulse rate and oxygen saturation, snoring pattern, position during sleep, respiratory efforts etc. with a closed loop control system (hardware). This embodiment allows for the automatic control of airflow pressure and/or air volumetric flow rate as in Auto CPAP or Bi-CPAP type machines without the need for external tube, wires, cords, fittings using proprietary algorithms built into the device unit command module.

The device brings airflow from the front of the mouth to back of the throat (pharynx area) and can be combined with mandibular advancement (bringing the lower jaw forward) to further assist in mitigating snoring and sleep apnea, referred to herein as PAP-MAD without micro-blower or CPAP-MAD with micro-blower or Auto-CPAP/MAD with closed loop control system.

The device may comprise the capability to record data by micro-SD card or wirelessly transfer data for real time monitoring and treatment compliance. The device can be controlled wirelessly using mobile devices.

One embodiment of the teachings comprises tongue depression design of hollow tube (or any hollow passage design). This serves two purpose: bring the air from outside to back of throat and same time keeping the tongue down, keeping more air passage open at the oropharynx area.

One embodiment of the device comprises of utilizing PVDF sensor technology with airflow and apnea/hypopnea detection already calibrated off the shelf strips (from Dymedix) or standard PVDF film strips that can be mounted in our device with proprietary algorithm to enable CPAP/APAP type operation for all the above PAP devices identified above.

One embodiment provides special design at back of the upper or lower arch of mouthguard which attracts the tongue to stay forward position during, keeping more air passage way open. One embodiment provides curve vertical semi-rigid plastics strip (fish tail shape) attached to hollow side tubes on both side, which pushes upper lip mouth area outward, keeping nasal air way passage open, helping further air coming from nose during sleep, reducing snoring and sleep apnea.

One embodiment of the teachings comprises providing micro-holes in the hollow tube (or hollow passage way), blowing air at very low flow rate, but stimulating the tongue to stay forward original position (does not allow to fall back) during sleep. These micro-holes can be near the tongue (lingual area) and/or at the end of throat area in a hollow tube (left and right) connecting the end of the two sides of hollow tubes of upper or lower each, directly blowing air to tongue and to soft palates of throat region. Slight disturbance of tongue and soft palate by air from these holes may be sufficient, not allowing soft tissues to relax, keeping air passage way open during breathing during sleep without waking up an individual.

Other embodiments envisage using nasal or oral-nasal delivery of air flow from device with or without auto control module and micro-blowers. One embodiment of the teachings comprises that the light source and pulse oximeter probe can be mounted outside the lip on vertical plastic strip which is part of hollow housing while the light detector is mounted on the mouthguard. Other concept of wired pulse oximeter can be mounted on ear lobe. Wireless pulse oximeter can be mounted on finger or any other location as done by conventional pulse oximeter. The information can be transferred to Bluetooth of the teachings device or Bluetooth of the smart phone or any such device.

One of the benefit of the device compared to current PAP machine is that there is no need to vent the air during exhalation since device allows to exhale thro' nose even when the micro blower is continuously blowing air during exhalation.

One embodiment of the teachings comprises special microchip embedded into mouthguard for nerve stimulation. The ultra-small neurostimulator, is mounted on the mouthguard (bonded to mouthguard or insert molded this tiny chip in plastic during injection molding of mouthguard). It's designed to be in close proximity to the nerves of the tongue muscle for stimulation. This reduces the tongue falling back during sleep, allowing more open airway passage.

Other embodiments envisage using nasal or oral-nasal delivery of air flow from device with or without auto control module and micro-blower(s). One embodiment of the teachings comprises an impact sport guard with additional airflow during the sports activity and protection of teeth. This embodiment is referred to herein as a positive airway pressure impact sports guard with or without micro-blower(s). This is accomplished by front housing having impact absorbing material or a 3-D printed lattice structure to absorb and distribute energy away from the teeth.

One embodiment of the teachings comprises that the light source and pulse oximeter probe can be mounted outside the lip on plastic which is part of hollow housing while the light detector is mounted on the mouthguard. Other concept of wired pulse oximeter can be mounted on ear lobe. Wireless pulse oximeter can be mounted on finger or any other location as done by conventional pulse oximeter. The information can be transferred to Bluetooth of the teachings device or Bluetooth of the smart phone or any such device.

The device can also be configured as a sleep apnea diagnostic device to detect OSA. For this use, the device has various sensors located in the hollow housing and/or the maxillary or mandibular arches which would be capable of measuring and recording oxygen saturation in blood and pulse rate (pulse oximeter), air flow rate, respiratory effort by Bluetooth/wifi enabled effort belts (RIP belts); temperature, position (tilt), Single lead ECG sensor packages with wireless connectivity can be used to monitor and record heart rhythm; also EEG sensors packages can be incorporated to monitor and record brain activity. Also inside mouth camera can be used to monitor changes in air passage. Proprietary algorithms can be applied to this data to determine AHI which could be correlated to standard Sleep diagnostic tests such as PSG or PG.

The device can be modified to serve as a sleep apnea diagnostic device. For this use, the device has more sensors located in the front outside housing and/or maxillary or mandibular arches such as differential pressure to measure air flow; pulse sensor to measure oxygen saturation in blood, pulse rate, temperature; a position sensor (tilt sensor) to indicate position of body while at sleep, Sound sensor to measure breathing variation and snoring; miniature video camera on the mouthguard to take pictures of inside of mouth during sleep; PVDF based sensor for air flow and temperature measurement; respiratory effort sensor (RIP belt). These data along with heart rate can provide information on AHI (Apnea Hypopnea Index) number for the individual (level of sleep apnea) as well as ability to discriminate between OSA and central apneas. EKG probes can be used for monitoring heart rhythm which can communicate with the device with wireless technology. Also additionally EEG sensors can be incorporated to measure brain activity and provide data on actual sleep time. The device can perform as diagnostic tool (as Home Sleep Testing (HST) or Out of center Sleep Testing (OOCST) for detecting OSA.

The device can also be used to titrate oral appliances such as mandibular advancement (MAD devices) and help select appropriate treatment without extensive sleep lab or home sleep testing. HST can be conducted with different mandibular advancement positions and the Diagnostic results from each overnight sleep study (HST) with different positions compared to select the best position for optimal treatment.

The device can also be configured with PVDF sensors applied to the patients' area above the lips and below the nostrils with a Dymedix sensor (previously calibrated) or with a PVDF film installed in the hollow housing and/or the maxillary or mandibular arches, with airflow and apnea/hypopnea detection capability to provide HST capability. PVDF film has a property that allows it to produce an electrical signal when variation in force, sound, acceleration, pressure, or heat is applied such as by airflow with varying temperatures (breathing in and exhaling), snoring sound, moving while asleep, etc. This signal can be captured and magnified by proper filters and amplifiers to produce waveforms as utilized by PSG/HST diagnostic devices and can be monitored and stored to provide and record indications of snoring, apnea/hypopnea and so on. The PVDF sensor would replace or enhance the sensors already indicated above.

In one embodiment the device can deliver compounds and or excite or stimulate appropriate nerves in the mouth to open air way passages. According to the present teachings, each device within the specification can be used with or without microblowers. Turning to the figures, FIG. 1A depicts an individual with no sleep apnea treatment device inserted in the mouth. Oropharynx area (upper airway) 15 is almost closed during sleep causing sleep apnea or snoring. In FIG. 1B, the same individual shown in FIG. 1A is depicted having a sleep apnea treatment device 13 according to the teachings inserted into the mouth, and oropharynx area 15 (airway passage) is less obstructed as air comes from the front of hollow housing of device and is delivered to the oropharynx area, completely bypassing air flow restriction areas such as soft palates, and tongue during sleep, reducing sleep apnea or snoring. Direct continuous air delivery during inhalation reduces sleep apnea occurrence as the airway passage is less obstructed.

FIG. 1C depicts a CAD drawing for the device 13. FIGS. 1D and 1E shows different designs of device. All FIGS. 1C, 1D and FIG. 1E having an upper arch can be customized using several mentioned methods. FIGS. 1D and 1E have sensors and/or microprocessor 127 mounted in the outer housing next to hollow airway passage opening. This sensor helps doctor to determine the patient compliance, sleep information and other parameters real time and/or over long period of time. FIG. 1C depicts a front top perspective view and FIG. 1E depicts a rear perspective view of one embodiment of the device of the teachings. As shown in FIG. 1C and FIG. 1E, device 13 comprises three main components: hollow front housing 110 with front opening 126 for air entrance and 127 space for microprocessor and sensors (for FIGS. 1D and 1E), hollow side tubes 115 which bring air from hollow opening 126 in hollow front housing 110 to oropharynx area 15 as seen in FIG. 1B and upper arch 100 which can be Non-customized or customized. Upper arch 100 can be made of single material or can comprise soft material 121 touching the teeth and semi-rigid material 122 on outside, facing lower teeth as shown in FIG. 1F. FIG. 1G shows the device 13 with strips to keep tongue down. FIG. H shows micro-processor and sensors attached to front housing.

Hollow side tubes 115 can be manufactured using the same materials as rest of device 13 or they can be manufactured from material 122 that is slightly more rigid than upper arch 100 material 121 as shown in FIG. 1F so they do not collapse, restricting the airflow. The rigidity of material also allows withstanding teeth grinding forces during sleep. By using a high modulus material, the wall thickness of hollow side tubes 115 and hollow front housing 110 can be in the range of 0.3 mm to 2 mm, the overall size of device 13 can be reduced, making device 13 more comfortable and increasing internal hollow space for airflow. Hollow side tubes 115 can be coated in their interior surfaces to reduce friction. Hollow side tubes 115 can be made of plastic material having low coefficient of friction, to minimize the air pressure drop from front air entrance area to exit at the back of throat area. Another primary cause of reduced air flow is turbulence, caused by the flow of the air when traveling in an indirect pathway. Where the air flow transitions, there should be a smooth transition curve which will result in less turbulence (smooth transition), so airflow will not be effected (laminar flow rather than turbulent flow). This will reduce the incoming air pressure drop, requiring less pressure need. Less air turbulence will also reduce air flow noise.

Hollow side tubes 115 can also have outer surfaces made of soft material for the comfort of the individual. The inside diameter (cross-section based on design) of hollow side tubes 115 can be constant or the inside diameter can be reduced slowly from front hollow housing connection towards the oropharynx/throat area to increase the air velocity, further aiding reduction of obstruction in the upper air passage. This also helps in increase response time when an Auto CPAP concept is used. As cross-sectional area decreases, air velocity increases inside hollow side tubes 115. The law of conservation of mass means that the size of hollow side tube 115 can be calculated to provide a desired air velocity using the following equation:

$$V_2 = (V_1 * A_1)/A_2$$

V is velocity and A is Area

Device 13 can be designed (figure not shown) to be used with a lower arch (lower teeth) only rather than an upper arch 100 as shown in FIGS. 1C and 1E. In this embodiment, the front hollow housing 110 (for air flow) and hollow side tubes 115 are attached to the lower arch of the mouth guard, eliminating the need for the upper arch mouth guard.

FIG. 1J shows few cross sections of device from front of the housing to oropharynx area (towards throat area) as per FIG. 1I. The cross section of hollow tubes or hollow air passage ways is determined by AHI index of an individual and required air flow rate and pressure.

FIG. 1K shows different designs of hollow tubes and hollow passage ways. The hollow passage ways can be in the form of tubes—round, oval, rectangular or any other size and dimension based on required airflow and pressure determined by hand calculation or by computational fluid dynamics (CFD). The hollow passage ways can be buccal side, lingual side or at occlusal area (between the upper and lower teeth). The hollow passage ways can be reduced in dimension from front to back. The length of hollow air passage way can be varied.

The hollow passage way can have micro holes at predetermined area from front to back just to excite tongue to stop it falling back, keeping air passage way open. The hollow passage way from two side tubes can be connected at the throat area having other hollow tube, creating "C" hollow section and there are holes only in tube at throat area to provide controlled air flow and pressure to reduce sleep apnea. FIG. 1L, FIG. 1M and FIG. 1N depict cross sections of one embodiment of a sleep apnea treatment or anti-snoring device 14 without micro-blowers having both upper and lower arches 100, 101 where hollow side tubes 115 are connected with upper arch 100. FIG. 1L and FIG. 1N depict a CAD drawing while FIG. 1M depicts the CAD drawing of an alternative design having micro holes which apply air to the tongue or soft pallet or throat area. Upper arch (maxillary) 100 and lower arch (mandibular) 101 of the device 14 have dimensions fitting upper and lower teeth of the wearer such that the device 14 does not move the lower jaw forward as would a MAD (mandibular advancement device).

Buttons or any snap fit design or matching tabs design on arches can be used to keep upper arch 100 and lower arch 101 of the device 14 together during sleep. Hollow front housing 110 comprises an opening 126 in the front of the device 14 where air enters and exits during breathing (inspiration and expiration). Hollow front housing 110 can be of any shape (rectangular, oval, square, round etc.) and is not limited to the shape depicted in FIGS. 1B to 1L. The size of hollow front housing 110 depends on the person's mouth opening size. For Non-customized devices, the size of hollow front housing 110 is designed in such a way that it will cover majority of the population having different facial dimensions, and can be manufactured in small, medium and large sizes. For customized devices, the device substantially fits the individual's teeth, but it is not necessary to cover all teeth as long as device does not come out during sleep.

FIG. 1O-1R show the sections of the device (fitting upper and lower arches/teeth) with front hollow housing opening having micro-sensors and microprocessor. FIG. 1N depicts an individual with full sleep apnea device while 1P depicts the device with a front portion removed, thus allowing for disinfection of only the moth portion, unsnapping the front hollow housing after the use of device.

The non-customized or customized device can be a single piece construction made out of semi-solid material, elastomeric material or hard/soft (soft in contact with teeth) materials. The device can be made by injection molding or/and two shot over-injection molding or insert injection molding processes or thermoforming processes, followed by bonding technologies as described earlier. Single piece design or two piece snap fit design with tubes (hollow air passage way), compact construction, fit, finish and comfort are the key factors used in the design, selection of materials and manufacture of the device.

FIG. 1Q depict air entrance opening 126 in hollow front housing 110 and air exit opening 130 from upper arch hollow side tubes 115 during inspiration. FIG. 1R depicts a cross section of device 14. FIG. 1Q depicts device 14 with hollow front housing 110 and hollow side tubes 115 attached to upper arch 100. Hollow front housing 110 can be completely detached and easily attachable at intersection 135, snap fit connection. FIGS. 1S-1Y represent various views of the device shown in 1O.

Further the top of housing part 110 can be split into 2 snap fit components if needed, permitting easy assembly and access for the electronics including micro-blower that will be mounted inside the hollow front housing 110.

The snap fit design (connect and disconnect of hollow housing from inner mouth piece) is essential to clean the device after every night and also to replace the inner mouthguard after few months as it wears out due to teeth grinding forces. Patient has to order only inner mouth piece and connect with original front housing to function like new device, reducing cost. For the customized "Boil and Bite" soft portion can be changed after certain usage if "boil and bite" is mechanical attached to rigid arch, further reducing the cost to patient and also frequent change reduces the bruxism or jaw deformation.

FIGS. 2A-2C depict one embodiment of a device 24 having air entrance opening 226 comprising a curved hollow air tube 230 connected from hollow front housing 210 directly to the center of upper arch 200, bringing air directly from the outside of the mouth to the back of the mouth. FIG. 2A, FIG. 2B and FIG. 2C and FIG. 2D and FIG. 2E are CAD drawings showing different views of the device 24. In this embodiment, the mouth has to be kept open slightly to permit the hollow air tube 230 to pass the teeth area and this is accomplished by putting tabs or spacer on bottom of upper arch and top of bottom arch or using the tube 230 to create this separation to allow pass-through. Here, spacer between upper and lower arch is built in (molded) to allow the center hollow tube pass through when device is inserted in the mouth, without touching the teeth. FIG. 2C depicts hollow tube without spacer can be used to separate upper and lower arch to direct the air flow from front of mouth to throat area. It works as spacer as well as hollow air passage way.

Curved hollow air tube 230 can be curved slightly downward so that it can apply pressure downward on the tongue such that the tongue does not fall backward during sleep, helping to keep the upper air way passage open (oropharynx area of mouth) and reducing the sleep apnea. Further the tube 230 will be flexible in the lateral domain to permit small sideways movement of the tongue for comfort. Curved hollow air tube 230 can be of any shape, round, square, rectangular. Curved hollow air tube 230 can be made of single material or multi-material where outside material is softer than internal material for individual's comfort. This concept can be used with or without mandibular advancement and with or without CPAP or Auto-CPAP having micro blower(s). The center hollow air passage way can be hollow spoon shape so that it can apply pressure on downward on the tongue, larger surface area than just the above mentioned hollow tube, further preventing the tongue to fall backward, helping even more air way passage open, and further reducing sleep apnea.

In one embodiment, curved hollow air tube 230 can be used along with hollow side tubes 215. FIGS. 3A and 3B depict one embodiment of device 34 to keep the tongue forward (not allowing the tongue fall back). If the device 34 is made to fit only the upper arch teeth or lower arch teeth, then multiple strips 340 can be joined accordingly as shown from left to right of the mouth guard arches 300, 301 (not shown in figure). Strips 340 can be straight, concave or convex. Strips 340 can be made of polymeric elastomer material. To stop the tongue from falling back, two sided pressure sensitive or moisture sensitive or any other chemistry type adhesive tape 350 in the form of small buttons or other shapes like rectangular tape can be used to cover the strip in whole or in part. Before placing the sleep apnea device 34 in the mouth, the adhesive buttons or tape 350 can be placed on one or more strips 340 by removing release paper on one side of the adhesive tape or buttons 350. Then, the other side of the adhesive buttons or tape 350 is exposed by removing release paper and the device 34 is inserted in the mouth. The adhesive of the adhesive buttons or tape 350 bonds to the tongue. The elasticity of adhesive and design of the adhesive buttons or tape 350 will allow some movement of the tongue from left to right or right to left, but will keep the tongue in a forward position, stopping the tongue from falling backward and keeping the airway passage open. Directional elasticity of the adhesive can allow significantly more movement of tongue from left to right or right to left compared to inward movement towards throat, not falling back. This will increase comfort level during sleep as some movement of tongue is allowed. It is also possible to hold the tongue in a forward position by putting the adhesive buttons or tape 350 at the back wall 315 of hollow front housing 310/arch 300, 301.

Figure 4A:
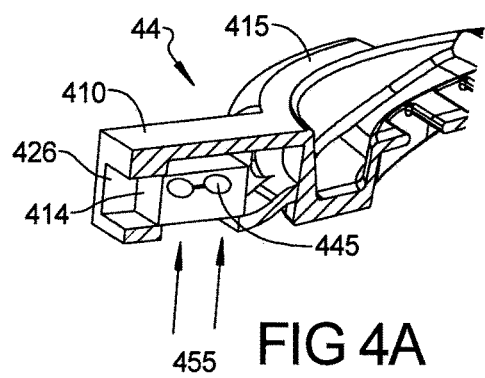
Figure 4B:
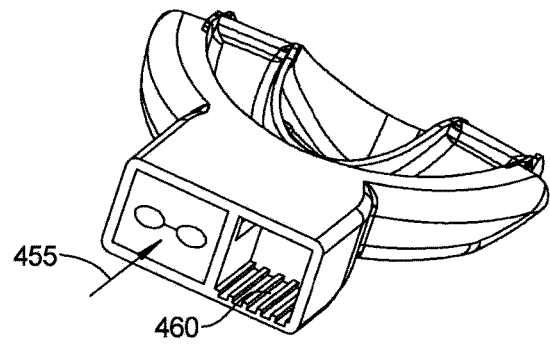
Figure 4C:
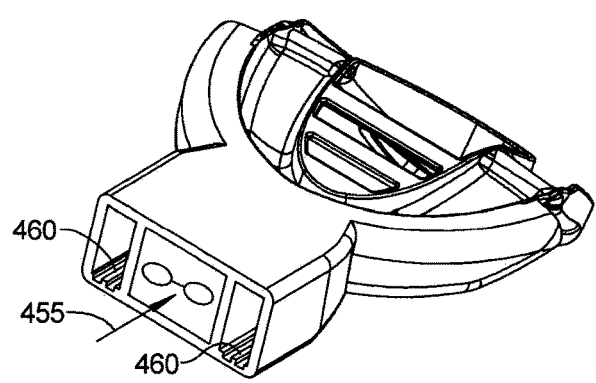

FIGS. 4A-4E depict a device 44 having micro-blower(s) 445 with continuous positive airflow (oral CPAP device) concept without automatic feedback control of pressure, flow rate, temperature, but with built-in microprocessor and sensors in device for compliance and monitoring purpose. FIG. 4A depicts a cross section of device 44 having Nano-fan(s) or micro blower(s) 445 with sensors/microprocessors etc. 455 is the direction of flow in the interior 414 of hollow front housing 410. Here, micro blower(s) is attached horizontally to front housing, bringing the air flow from bottom of the hollow housing. While FIGS. 4B and 4C shows device where micro-blower(s) is mounted vertically, bringing the airflow directly from front housing to hollow tubes or hollow air passage way. This is most preferable way of mounting the micro blower(s) since this attachment provides less resistance to air flow and less flow turbulence. This design also provides ease of device manufacturing. But, in few types of micro-blowers, vertical mount may not be feasible. Sensors, microprocessors, USB drive, batteries etc. are inserted in open chamber 460 of the front housing next to micro blower opening in FIGS. 4B and 4C. Device 44 is depicted in FIGS. 4A, 4B and 4C having micro blower(s) 445 in the interior 414 of hollow front housing 410 having sensors, microprocessor, batteries and USB card, Blue tooth port etc. The mounting of these sensors and other items are discussed in FIG. 7. The dimensions of the walls of the hollow front housing 410 depend on the type of material and manufacturing process. The dimensions of opening 426 of hollow front housing 410 vary depending on the type and number of micro blowers 445 that are used. When micro-blowers 445 are inserted when opening 426 is in the front of hollow front housing 410, micro-blowers 445 have a tight fit with the inner wall of hollow front housing 410. Elastomeric/rubber gasket can be used to prevent or minimize air leakage. As shown in FIG. 4A, micro-blowers 445 rest on bottom walls on both sides of hollow front housing 410 having bottom opening 455 for air entrance. Gasket material can be used to seal the front opening 426 of the hollow front housing 410 around the wall of micro-blower 445.

Figure 4D:
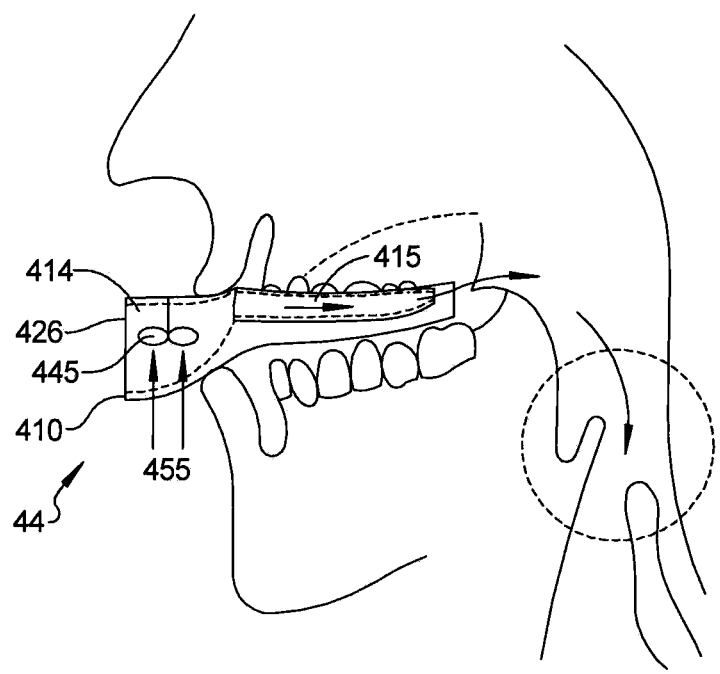
Figure 4E:
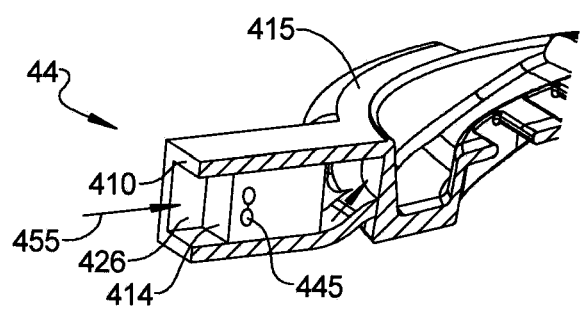

The front or bottom opening 455 of hollow front housing 410 allows for air flow for micro-blowers 445. This way, during inhalation, as micro-blowers 445 turn on, air comes in from the bottom opening 455 of hollow front housing 410, exits hollow front opening 410, moves other side of micro-blower(s) and then moves into hollow side tubes 415, directing air directly at the oropharynx area. It is possible to increase the pressure or velocity of incoming air by reducing the size of the hollow side tubes 415 from the entrance at the hollow front housing 410 to the exit in the oropharynx area. It is also possible to change the pressure and flow rate of incoming air by changing the voltage supply to the micro-blower(s). The arrows in FIGS. 4A, 4B, 4C, 4D and 4E show the airflow directions from opening of the hollow front housing 410 through micro blowers 445 to the hollow side tubes 415 to oropharynx area (throat area) and can have a 3 to 5 times the tidal volume. Only difference is that micro-blower(s) are mounted vertically, directing the air flow straight into the hollow tubes or hollow passage way in case of FIG. 4B and FIG. 4C. FIG. 4B shows embodiment with micro-blower mounted vertically and allowing for straight air flow to back of mouth. FIG. 4D depicts a person wearing this kind of oral CPAP device.

The design of device 13 envisages placement of the micro-blower at center FIG. 4A and FIG. 4C or on the side of front hollow housing as shown in FIG. 4B When the blower is placed on the side as opposed to the center, the dimensions on both tubes or either hollow passage on device inside the mouth will be adjusted to get even flow rates from both hollow passage discharges of air at back of mouth (oropharynx area).

This continuous positive airway pressure oral device (PAP or CPAP), provides unobstructed breathing by delivering a constant flow of air through the side tube(s) or center tube(s) or any other hollow air passage designs connected to the front hollow housing, directly to upper air passage way. The oral device with housing is designed such a way that when individual wears it, it is secured to the lips so that little or no air escapes from the front. Also, the micro-blower(s) are constantly running, so exhalation will mostly occur through nose. Due to this constant level of airflow during inspiration, air pressure, air flow and air velocity increases in the oropharynx (throat area) so the upper airway does not collapse during inhalations while sleeping. Air flow from the micro-blower can be adjusted by control module as required.

Although this is not an Auto-CPAP type device but only a CPAP type device, the device can adjust the micro-blower output to match inspiration and expiration cycles based on temperature sensors, if needed but constant running of micro-blower(s) is preferred.

A variety of suitable micro-blowers are shown in FIGS. 5A-5D. Depending on the individual's requirement (based on sleep study), a specific micro-blower type and size can be selected to have fixed volumetric air flow rate up to 30 liters per minute and/or air pressure of up to 30 cm H20 (3000 pascal). It is possible to change (set) the pressure and volumetric flow rate of the same micro-blower manually. A CFD (computation flow analysis) will be used to determine and demonstrate the efficacy of the device under various design parameters and biological physiologies.

Micro-blowers with different mechanisms can be used including but not limited to the following: The micro-blowers can be based on concepts such as Piezo-nanofan 570 shown in FIG. 5A. The Piezo nanofan consists of blades made of stainless steel, brass or even Mylar. Attached to the blades is a patch of piezoelectric ceramic material. Piezo-electric material deforms in the presence of a voltage field. Positive and negative electrical voltage affect the material differently. As a positive voltage is applied, the ceramic can expand, causing the blade to move in one direction. A negative electrical voltage can cause the ceramic material to contract and move the blade back in the opposite direction. The fan's speed can be adjusted by changing the frequency of the current. The nanofan or micro blower can be based on axial air gap technology 571 as shown in FIG. 5B with almost no power loss. One can use roots blower 572 as shown in FIG. 5C, a more positive displacement pump. One can use a micro-blower concept using-Air Multiplier 573 as shown in FIG. 5D (powerful airflow, no blade). The Air Multiplier is a blower with an unusual characteristic in that it does not have any visible blades. It appears to be a circular tube mounted on a pedestal. The shallow tube is only a few inches deep.

One can use centrifugal fans, of which there are 3 major classes—forwardly curved, backwardly curved or straight-bladed. They generally move less air but at a higher pressure. Some fans are called compressors if they turn at sufficient speed to materially compress the air they are moving. Centrifugal fans are usually mounted in a housing that looks like a snail shell. The inlet is in the center and the discharge is the opening of the shell at the outer edge of the scroll. When the blower is integrated with a housing and a motor, it then becomes a blower.

One can use a plurality, such as hundreds, of Nano blowers instead of micro-blowers inserted into the hollow housing of the device. In case of an SAT (sleep apnea treatment) or AS (Anti-snoring) device with several nano-blowers, it is possible to generate the full range of treatment pressures up to and in excess of a treatment number of 20 cm pf $H_2O$, because of the strength of the electrostatic force that drives the nano-blower plates, like bellows, open and closed, together and apart. Each nano-blower can push a small amount of air at significant pressure, and hundreds of nano-blowers work in parallel to achieve the required volume to effectively treat the particular individual's sleep apnea. Due to significantly less air leakage and pressure drop, the individual may not need to have this high treatment number of pressure 20 to 30 cm of H2O (current CPAP machine—30 cm of H2O or up to 3000 pascal), but can be achieved in case if it is needed. To reduce cost, these micro or nano-blowers can be manufactured by "roll to roll" (R2R) or similar low cost, high volume manufacturing processes. Since, oral CPAP innovation directs air directly from front of the housing to oropharynx area, bypassing the tongue and soft pallets, the pressure required is significantly low compared to current CPAP devices. CFD data shows that 2 cm of H2O can be sufficient, not 20 to 30 cm of H2O required for traditional current CPAP machines. This is a great advantage since it will significantly reduce the numbers of Nano blowers compared to nose mounted CPAP device, or less powerful or less number of other micro-blowers described above.

The dimension (sizes and shapes) of the hollow front housing of the device depends on the type and size of micro-blower(s) and also for a specific individual and face size or there can be three sizes offered (small, medium and large).—For example, a micro-blower is shown having dimension of 17 mm×17 mm×8 mm fan, having volumetric airflow of 30 liters per min (500 ml per second). Tidal volume (air volume displaced during inspiration or expiration) without extra effort is 500 ml during inspiration (for breathing). A typical respiratory rate for an adult at rest is 12 to 20 breath per minute, meaning each breath (in and out) is 3 to 5 seconds. For example, given 2.5 seconds inspiration time (breath), tidal volume is 500 mL. For inspiration time of 2.5 seconds, air volume taken in is 500 ml (200 ml per second).

If this micro-blower is used (having capacity of 1 CFM=30 liter per min=500 ml per sec), air volume can be 1250 ml (500 ml×2.5 sec) per inhalation, increasing the airflow rate by 2.5 times then required in normal case. For patient suffering for sleep apnea, this will open the air passage in the oral cavity significantly and prevent the collapse of soft tissues in oropharynx and larynx, preventing mild to moderate sleep apnea and snoring. By using hollow tubes taking air directly to pharynx area, air is brought in faster where needed, even further reducing sleep apnea and snoring event of patient. If one micro-blower does not perform as needed, more than one micro-blower in series can be used to get more airflow and pressure.

FIGS. 6A and 6B depict an Auto CPAP (APAP—Automatic positive air pressure) device 64 with Miniature Auto Control Module 605 inserted in hollow front housing 610 along with micro-blower(s) 645 and sensors 646. 605 can be mounted horizontally or vertically depending on the type of micro-blower(s) used. FIG. 6C depict micro-blower(s) 645 and automotive control module are mounted vertically in front housing. Control module 605 is data-capable and records all information on events and compliance. Control module 605 having a microprocessor with several sensors 646 and micro-blower(s) 645 is placed directly in hollow front housing 610 of a single piece and may provide variable flow depending on the response measures and calculated by the controller. Micro, oral device 64 having very small space in comparison to current Auto CPAP devices where the control module 605 along with blower/motor 645 is located remotely from the individual and airflow is brought through a hose or tube to the nose or mouth or both. Vertical mount of micro blower may allow to reduce overall size of the device.

The microprocessor or micro-chip in control module 605 is in communication with airflow (differential pressure), temperature, tilt, sound sensors and pulse oximeter 646 to provide continuous feedback of changes in any parameters to microprocessor. Sensors 646 not only can be attached to control module 605 but also to the mouth guard (inside arch 600), further increasing the capability of device 64 for sleep apnea and also other purposes such as diagnostic device as well as compliance information. Based on the history and AHI index, the microprocessor automatically adjusts air flow rate/pressure to improve the comfort level of the patient. To reduce further discomfort and also keep air passage way open for longer time, micro blower(s) may not be supplying air flow continuously. This is achieved by using a thermistor sensor in 646 which monitors the individual's breathing and send an output that reduces the flow of the device 64 internal blower when the individual starts to exhale. The exhalation temperature is higher than inhalation temperature. The resulting lowered resistance prevents the individual from feeling as though he is "fighting" against the machine when breathing, reducing discomfort.

The control module can be mounted inside the front hollow as shown in FIGS. 6A and 6B or also can be mounted on the top portion or bottom or side portion of the housing. Also it can be split into multiple PCB's with varying configuration. Pressure sensors can be used monitor the pressure delivered to the individual in all type of PAP machine types.

Analog Temperature Sensor (breathing timing sensor) is a small package thermistor which can be used for a fast response. This sensor can be placed in a location where it can be contacted with exhaled air. Analog temperature sensors provide a signal to the microprocessor indicating the start of the exhalation and inhalation cycle. The exhalation temperature is higher than room temperature, indicating start of exhalation, giving feedback to microprocessor to control micro-blowers. Start of inhalation is sensed by temperature or/and air pressure sensor.

A customized or Non-customized oral Auto CPAP type (automatic positive airway pressure) device continuously monitors the sensor parameters and utilizing proprietary algorithms automatically varies the air flow or pressure as per individuals need. APAP adjusts the air flow (pressure) to improve upper airway passage opening to a comfortable level, not too much pressure or airflow then required.

Through the use of firmware (proprietary algorithm) on the control module, the device automatically controls the air pressure and airflow rate by continuously changing air micro-blower's speed using closed loop control system. It is not necessary that individual has to have all teeth, so long as the device can be held in the individual's mouth by a few teeth. The device has a fast-response micro-blower(s), pressure transducer and microprocessor. The device control module discerns stoppage or blockage of breathing from data being collected from the various sensors and will accordingly adjust the air flow (pressure) from the micro-blower to varying preset values as per the proprietary algorithm. As discussed in connection with devices without micro-blowers, the Auto-CPAP device with micro-blower can be attached to upper arch or lower arch, or attached to both arches with or without moving lower jaw forward (like a MAD device). There is also an air filter (washable or disposable) that can be attached in front of the micro-blower to filter dirt. Hypoallergenic disposable filters are made of non-woven acrylic and polypropylene fibers with a polypropylene carrier. The combination of materials helps block very fine particles, and some filters claim to have anti-microbial agents. The hollow housing can be made of plastics having anti-microbial agents (with or without controlled release).

The micro blower and microprocessors etc. can be powered by coin type or other types of micro-battery or rechargeable (electric or USB type) coin cell or other types of micro-battery such as a polymeric micro-battery. Data storage and transfer can be achieved by a variety of technologies, thus eliminating need for any cord or wires. Two such technologies include Bluetooth® and micro-SD card. The device may incorporate Bluetooth® technology such that the device is continuously synced (or synced whenever desired) with any other Bluetooth® enabled mobile device such as smart cell phone, tablet, computer etc. The mobile device can then up link through the Internet to send the data from the device to an Internet server. The device can then provide sleep apnea related data to a device having an appropriate app, which data can then be analyzed and stored on the device and/or can be communicated/shared with doctors or other medical professionals or other third parties via email or via cloud. Using a smart phone or similar devices, it is also possible to send input to control module of the device to set up initial required air flow (pressure) etc. for individual as needed.

Micro-SD card: The micro-SD card can store all sleep apnea data during sleep and can be downloaded to a device such as a smart phone or computer at a later time. Other configurations of the device can include Wi-Fi capable. Additionally, the control module may have the capability to manual control if needed and OLED to show the state of the system. The control module may use an algorithm that learns from individual's breathing pattern and reduces device pressure on exhalation (expiration). Sound output from the device will be between 12 to 18 dBA during normal operation. By CPAP industry standards that are considered to be exceptionally quiet. Auto-off function puts the display backlight to sleep Functions offered on current CPAP devices can also be incorporated into this oral CPAP device or on mobile app to a connected mobile device with display for power status, pressure and ramp time. It also gives audio visual feedback when programming ramp and pressure settings.

FIG. 7A depicts the cross section of an Auto-CPAP (APAP) front hollow housing with micro blower 760 and control module 735 consisting of various elements inserted in the hollow front housing of a device that is in communication with mobile devices 770 to download (sync) the data. Elements include but are not limited to: LCD and touch screen control 700 and on/off switch 701 Bluetooth® sensor 705 and micro-SD card 710, pressure sensor 715, airflow sensor 720, temperature sensor 725, sound sensor 730, and tilt (position) sensor 732, microprocessor with firmware 740, rechargeable battery with USB port 745, material or fabric with high water absorption capability during exhalation and desorption during inhalation 755, micro-blowers 760 and air filter 765. The sensors may be positioned differently than shown inside the mouth in the mouthguard or alternate locations as required. 770 depicts a mobile device in communication with Bluetooth® or other wireless communication link 775 mounted with a sleep apnea device comprising a control module. 785 depicts the respiratory belt (RIP) belt. 780 depicts pulse oximeter that will also communicate with the control module via Bluetooth or other wireless methods. A material 755 is incorporated after the microblower to absorb moisture of exhalation.

FIG. 7B depicts a schematic of the control module of a device to treat sleep apnea and snoring. The device has proprietary firmware/algorithm to operate in different modes such as CPAP, Auto CPAP, Bi-CPAP etc. Method of operation of a single piece tubeless Auto CPAP oral device: The control module is programmed with firmware/algorithm to perform the following operations as shown in FIG. 7B. The individual puts the oral device in his/her mouth, fitting it well, and then turns the on/off switch 701. The device can also be turned on using a connected device such as a smart phone 770 via Bluetooth® 705. The start of inhalation can be detected by setting a pre-determined value for temperature sensor 725 (less than body temperature) or air pressure sensor 715 (atmospheric pressure). Air enters when the micro-blower 760 starts during inspiration via a signal given by the microprocessor 740, based on input from temperature sensor 725 and/or pressure sensor 715. The air is filtered by filter 765 before entering in the hollow front housing 610. A material 755 incorporated into the control module area 605 has high water absorption capability from the surroundings. If needed, this material 755 can be soaked in water and incorporated in the hollow front housing 610 before sleep to achieve a level of humidity.

This material 755 does not affect the air flow due to its location in the hollow front housing 610, but at the same time it picks up moisture during exhalation. Moisture is then released in air during inspiration, the amount of moisture depending on air flow rate and temperature. The humidity level does not alter the pressure level or change the therapeutic value of CPAP device, it just improves the comfort. Due to the relatively tight seal of the device at the lips, there is little or no leakage and the individual can also breathe through the nose. Also, since the micro blower(s) are continuously running, air is always entering thro' mouth during inhalation and exhalation. As air always enters thro' mouth via micro blower, person more likely to exhale through nose, thus there is no need for tight seal of oral device at mouth.

The RIP Belt 785 and Pulse Ox 780 will continuously send data about respiratory effort and oxygen saturation as well as Pulse rate via wireless methods to the control module and which can then be recorded on the storage device. Sensors read pressure and flow rate values and once they deviate from predetermined set values, they provide input to the microprocessor 740 of the control module 605 which in turn changes the micro-blower 760 speed up or down (changing the power supply level). The control module 605 is operable to determine the occurrence of an apnea from a reduction in respiratory airflow below a threshold, and if an apnea has occurred, to determine the duration of the apnea and to cause the flow generator (micro-blowers 760) to increase the treatment pressure/flow rate by an amount which is an increasing function of the duration of the apnea, and a decreasing function of the treatment pressure/flow rate immediately before the apnea.

The start of expiration can be detected by temperature sensor 725 or air flow sensor 720 or sound sensor 730. During expiration, the speed of micro-blower 760 can be reduced to decrease resistance to airflow during expiration, for increasing comfort. Data-recording devices such a micro SD card can be used to record multiple variables from the sensors described in FIG. 7 or can be wirelessly uploaded to servers. This will help to determine optimum pressure, but the most common measurement is individual's "Apnea/Hypopnea Index" or "AHI", where the goal is to get AHI to 5.0 or lower.

The same Auto CPAP device can also be used as BiPAP/VPAP by changing the algorithm of the firmware on the control module to have different modes of operation during sleep as described below. Bilevel-PAP (Bilevel Positive Airway Pressure) provides two levels of pressure: IPAP (Inspiratory Positive Airway Pressure) and a lower EPAP (Expiratory Positive Airway Pressure). Bilevel or variable level machines (BiPAP/VPAP) blows air in two levels, one for inhalation (IPAP) and one for exhalation (EPAP). This method is used in situations where marked difficulty breathing is present.

These devices can be available a) either in a range of air flow/pressure values so that individual will be able to obtain the device with the treatment number appropriate for him/her, much like contact lenses or b) device will be made adaptive so that they will self-adjust (like some current high-end APAP machines) to provide the exact pressure for effective treatment FIGS. 8A-8B depict the same concepts for the devices as above in FIGS. 6A-6D and 7A-7B but the single piece micro oral tubeless device 84 has capability of bringing the lower jaw forward (mandibular advancement) in the same manner as MAD devices 80 as seen in FIG. 8A currently in the market by opening of the mouth upper airway passage area (oropharynx area). As seen in FIG. 8A, current MAD devices 80 lack a hollow front housing, microblowers or hollow side tubes in the mouth guard upper and lower arches 800, 801. Oral MAD CPAP device 84 shown in FIG. 8B and FIG. 8B consists of CPAP module 805 (same as 605 in FIG. 6A) incorporated in hollow front housing 810, with hollow side tubes 815 (same as 115 in FIG. 1D) to deliver air directly to oropharynx area and design mechanism 880 as an example to bring the lower jaw forward.

The lower jaw, mandibular, can be moved forward by other mechanisms available in the market. The single piece micro oral MAD/CPAP device design mechanism 880 allows the mandible to be advanced in increments of 1 mm or less with a protrusive adjustment range of at least 5 mm. In addition, reversal of the advancement is possible. The protrusive setting is verifiable. It maintains a stable retentive relationship to the teeth, implants or edentulous ridge and retains the prescribed setting during use. This concept of mandibular advancement (MAD) can be used for customized or Non-customized device and also for CPAP, Auto-CPAP, Bi-PAP devices etc., along with other features/concepts described for other embodiments of the teachings as described herein. The current MAD devices on market, essentially only bring the lower jaw forward by methods such as Herbst, TAP, EMA (strap) etc.

These current devices do not have any capability of measuring any parameters of air flow during sleep or providing any titration data or functioning as a CPAP or APAP. Teachings Device shown in 8B has all the capabilities (including the electronic package of command module and sensors) of all embodiments described earlier plus the capability of mandibular advancement using various methods as shown in FIG. 8A including variations to those indicated above (Herbst, TAP and EMA) to achieve this.

This oral device can have electrical stimulation capability for providing mild shocks to the soft palates and tongue. When the electronic sensors detect blockage of air passage (by soft palates relaxing or when the tongue falls back and blocks the airway passage), the device can provide a mild electrical stimulation, and alleviate the blockage of airway passage from persisting further due to above events.

It has been proven that side sleeping position reduces the sleep apnea events by more than 20%. When individual moves from side position to subprime position, the tilt sensor records it and the built-in proprietary algorithm (software) sends a signal to thin plastic sheet (or a patch on face) attached to the device and touching to lip(s) to vibrate. This reminds individual to sleep on side. The individual slowly adjusts to this and over few nights adjusts to sleep on side without waking up. One of the appliance designs is very simple that it will be just upper mouthguard with outside housing having tilt sensor to remind the individual to sleep on side.

This device can be used as impact sport guard with additional airflow during play and protection of teeth. It is referred to as a positive airway pressure impact sports guard without micro-blower(s). Such impact sport guards have a hollow housing in the front with two hollow side tubes attached to upper arch of the device. They can also be used for people in contact and non-contact sports acting as a protection mouth guard as well as a device to increase air intake, just like breathing deeply without the thought and effort. The impact blow abruption and dissipation characteristics are achieved by making device using additive manufacturing (3D printing) technologies with lattice structure.

FIG. 9 depicts a nasal/oral device 94 with CPAP/MAD or Auto CPAP Device/MAD. This nasal/oral device 94 can also be used without mandibular advancement (without MAD). Internal hollow tubes inside the mouth (on upper or arches) can be blocked or eliminated in the oral device (no air flow going through the mouth), but two hollow flexible conduits 916 are connected to two nostrils from the top of the hollow front housing 910 of oral device in which micro-blowers 945 are attached; or the airflow can be from both nose and mouth if the internal mouth tubes are left open. This can be achieved by nasal elastomeric housing 990 (Like nasal pillows used in CPAP machines) snug fitting the nose where conduit 916 are coming out from the oral PAP device 94. The end of each of the two tubes 916 has an expandable elastomeric attachment or nasal cannula 995 or nose pillows for each nostril, snug fitting inside the nostrils which holds the two tubes 916 and nose housing 990 in place during sleep.

The nasal cannula can also be kept in place by using strip around the ears. The oral device 94 has two functions: 1. the hollow front housing 910 with micro-blower 945 delivers air flow to nose by itself or along with the airflow through the mouth during inspiration instead of inside mouth 2. The oral device 94 holds the nose housing 995 with control module, micro-blowers 945 and sensors and tubes 916, the whole air delivery system, in place as device is attached to teeth (upper or lower or both upper and lower aches). This oral device 94 can have a mechanism to bring lower jaw forward (MAD device), further opening the air passage way in mouth.

This device 94 allows reduction of sleep apnea by providing natural air flow through nose (natural breathing) in combination with lower jaw movement (nose CPAP or APAP with MAD Device). The elastomeric housing 990 snug fitting the nose have micro holes allow and controls the airflow during the expiration. Airflow from the hollow front housing 910 can also be controlled during the expiration by reducing the speed of micro-blowers 945 if expiration should be slowed down. Note for Nasal airflow the technique to increase humidity is described earlier in FIG. 7 while inhaling will be used.

Micro-Nasal PAP device: In a specific embodiment of the device, it can be attached directly to nose with microprocessors and sensors. This nasal micro PAP device has external housing, snug fitting with nose with two hollow tubes going into nostril. The external housing has micro blowers or nano-blowers with similar concepts of control module with pressure and flow rate sensors as described previously for the oral PAP devices (FIGS. 4A-4D or FIG. 6B). It is a stand-alone single unit like oral device but attached to the nose instead of mouth. The device has no external tubes or cords.

A fabric or film with directional nano pores structure can be disposed in front of the oral or nasal device to slow expiration. The device can have breathable anti-microbial fabric or film with directional nano pores structure with or without micro-blower SA or AS device. This fabric can be placed in front of the hollow box where air enters into the mouth or nose during inhalation. This fabric can be adhesively bonded, or can be permanent or preferably removed every day to wash or insert same one or new one (every moth) before using device. As the individual breathes in, the fabric or film's nano structure design opens the pores, allowing the individual to breathe in normally. Then, as the individual breathes out, expiration is slowed as the nano structure pores closes slightly to create a gentle pressure that naturally opens the airway and relieves snoring or mild to moderate sleep apnea.

The data acquisition capability of the oral devices of the various configurations described above (FIG. 7A and FIG. 7B allows it to be used as a diagnostic device for sleep apnea for diagnosis of Sleep Breathing Disorder—specifically obstructive sleep apnea and allows to set parameters for current CPAP machines or device of current invention. This oral HST device can essentially function as a stand-alone HST (Home Sleep Testing) or OOCST (Out of Center Sleep Testing) device such as Resmed's Apnea link or Itamar's Medibyte and so on. In the present system, it can be used to set parameter of oral sleep apnea device of current teachings.

The device is a multi-channel screening tool, that can measure all or selected parameters such as airflow through mouth or nose, snoring, oxygen saturation, pulse, temperature, body position, respiratory effort during sleep, EKG, EEG by various sensors that are built into the device or linked via wired or wireless technologies such as Bluetooth or Wi-Fi.

The acquired data from this device can be used to calculate apnea-hypopnea index (AHI) based on the sleep time recorded based on proprietary algorithm which can generate a comprehensive sleep study report with a custom app or software. This AHI determination with other parameters recorded would permit prescribing/specifying appropriate CPAP/APAP/BiPAP treatment option (setting appropriate pressure (and/or air flow rate) for PAP or pressure range (and/or air flow rate) for APAP devices as well as MAD (Mandibular Advancement Device) treatment option (setting the position of the lower jaw advancement). The device can also have a miniature/nano IR or thermal imaging video camera which can help detect changes in the airway passage during sleep.

In one embodiment of the device, it can be used to validate the mandibular advancement device (MAD) setting used for treatment of OSA and snoring (OS/SA). In this version, the device would have all sensors mentioned above or limited sensors and built in capability on the control module to discriminate the efficacy of the MAD treatment and validate the lower jaw advancement setting selected. If used limited sensors, it would have 3 indicators that would indicate if the efficacy of the MAD treatment made a positive difference (ie reduce the OSA/AHI or reduced snoring) or made no difference or made a negative difference and made the symptoms worse. The indicator can be a color coded system (such as green/yellow/red) or light up different labelled lights to depict the 3 outcomes. The efficacy of MAD device can be also be shown as actual AHI index number.

The devices can be of any constructions/concepts as described previously but not limited to: 1. only upper arch or lower arch device or device with both arches 2. Both upper and lower teeth arch without bringing lower jaw forward 3. Both upper and lower teeth arch where lower arch is adjustable to bring lower jaw forward, 4. Center hollow tubes/hollow passage ways or strips or any other design to keep tongue down.

The various embodiment of the device described above also work as night guard to prevent bruxism, teeth grinding and also treat TMJ in addition to reduce snoring and sleep apnea.

FIG. 10 depicts thin plastic bag attached to upper arch of mouthguard (at the end, throat area) which expands and stays expanded during air flow from micro blower, stopping soft palates to collapse, allowing more open airway passage. If device has no micro blower, during normal breathing this bag will expand during inhalation and collapse during exhalation but stays in place due to specific bag design and support design with upper arch. It is also possible to have dome same semi-rigid plastic bonded with upper arch which will not allow the soft palate to relax, keep in place during sleep.

The Non-customized device or customized devices (to fit individual's teeth) are supplied in different sizes such as small, medium and large. The device can be made by snap-fitting injection molded hollow front housing with rest of the part—hollow side tubes and upper and lower arches (mouthguard). This way hollow front housing can be easily detached from rest of the device after sleep to clean the mouthguard or when required such as repairing or replacement.

FIG. 11 depicts an exploded view of device as separate pieces which are snap fitted together after manufactured. 1110 is front housing and 1120 is inner mouth piece. 1111 is partial hollow tube and 1112 is base of mouthguard. While 1113 is "boil and Bite" piece on top of base piece of mouthguard 1112 for customization.

FIG. 12 depicts several manufacturing methods for device. Both non-customized and customized devices consist of two pieces A and B as shown below: front hollow housing 1210 (in which micro fan(s), sensors, microprocessors etc. are inserted after manufacturing); and an inner mouth piece 1220 with hollow air passage way. The front housing has snap/un-snap fit concept where front hollow housing section is easily snap-fitted with inner mouth piece and also can be easily un-snapped (removed from inner piece).

The systems can be formed using the following methods. The front hollow housing 1210 is made by injection molding. To prevent air leakage between hollow housing and inner mouth piece, an elastomeric ring is mounted on front housing or elastomeric ring is molded in one step process as two shot injection molding. For the inner mouthpiece 1220, the following manufacturing methods are used to achieve predetermined hollow passage ways. The inner mouth piece is divided into two portions: 1. Partial hollow tube 1211 and 2. Base piece of Mouthguard 1212 (upper or lower arch) A multi-step process can be used which includes separately injection mold partial hollow tube 1211 and base piece of Mouthguard 1212 followed by bonding these two pieces to create hollow passage way in inner mouth piece 1220.

One can also make partial hollow tube 1211 and base piece of Mouthguard 1212 by thermoforming process followed by bonding these two pieces to create hollow passage way in inner mouth piece 1220. Thermoforming process allows for customization. Bonding of these two pieces can be done by ultrasonic welding, laser welding or mechanical bonding or combinations of these technologies or adhesive bonding or other bonding technologies, creating the thin device with hollow side tubes. The wall thickness can be as low as 0.5 mm in several areas. One step injection molding process where partial walls of tube 1211 and base mouthguard 1212 are molded in two cavities of a single mold, followed by rotating cavities where two halves are aligned and second material 1213 is injected at intersection, bonding these two pieces and creating hollow structure. Here, the second material 1213 is soft material or same as "Boil and Bite" material 1213, creating customized oral device in a single step process. (see FIG. 15). Water or gas injection molding to achieve hollow air passage way. Lastly, lost core foam injection molding can be used to for the passages.

Both non-customized and customized devices are manufactured by similar processes as described above except for customizations (to fit the teeth perfectly) is achieved by processes such as 3D printing (hard or hard/soft materials), "boil and bite" concept and micro-cellular foaming injection molding processes and thermoforming of a plastic sheet on a tooth model. The device can be single piece construction, if it device does not contain any sensors/microprocessor or sensors/microprocessor and battery are completely sealed, then no need to have snap-fit feature. This single piece construction can be achieved by bonding of two separate injection molded halves at pre-determined line (or separately injection molding hosing with partial tube and mouthguard) followed by bonding these two pieces to create hollow structure or by water injection molding or by lost core foam injection molding. 3d printing or additive manufacturing can be used to form the components or single piece device.

Figure 13A:
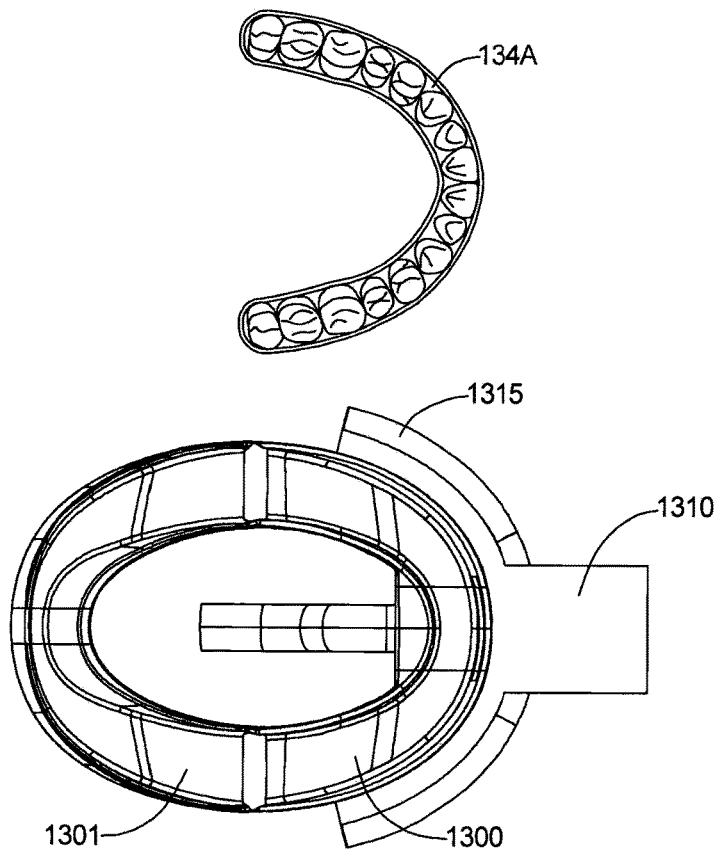
Figure 13B:
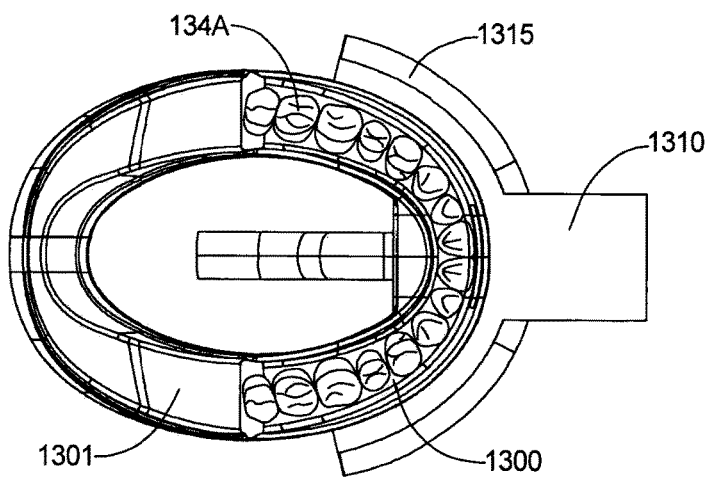
Figure 13C:
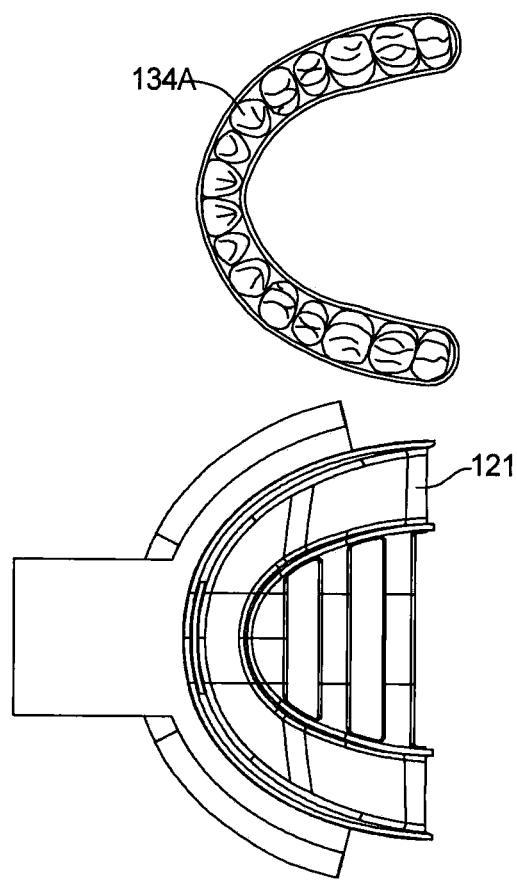
Figure 13D:
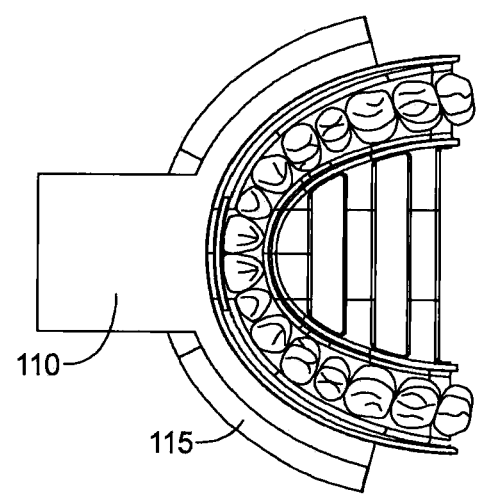

FIGS. 13A-13D depict a customized cross sections of the device using "Boil or Bite" concept to fit individual teeth. FIG. 13A and FIG. 13B depict portions of a device 134A, having both upper and lower arches 1300, 1301 with hollow front housing 1310 and hollow side tubes 1315 attached to upper arch 1300. FIG. 13C and FIG. 13D depict a device 134B having upper arch 1300 only with hollow front housing 1310 and hollow side tubes 1315. Upper and lower arch portions touching the teeth are made of material which will soften on boiling in water, due to glass transition temperature of lower than 100 C and will form to the shape of teeth upon biting in the mouth. The arch portions may be made of single soft material or soft and hard material. Soft material is used for "Boil and Bite" and hard material provides the support during bite. The hollow front housing 1310 and hollow side tubes 1315 (and bottom of upper and lower arch portions) are made of high temperature plastics which do not soften at all at 100 C (boiling point of water) due to their glass transition temperature greater than 100 C. This way, after "Boiling and Biting" the device 134A, 134B, the individual can customize the device to fit his/her teeth and still air flow will not be affected as rest of the dimensions of device will not be changed during boiling and biting (hollow tubes and the hollow housing dimensions).

The "Boil and Bite" devices can be manufactured by two methods. 1. First, "Boil and Bite" soft portions of the upper and lower arches are injection molded (or two-shot injection molded from soft/hard material) and this portion is inserted in a second tool where it is over-molded with high temperature plastics material forming rest of the part having hollow side tubes and hollow front housing or 2. "Boil and bite" portions of upper and lower arches and rest of the device (hollow side tubes and hollow front housing and bottom arch) are injection molded separately as shown in FIG. 13A or 13C, then mechanically snap-fitted to make a single device shown in FIG. 13B or 13D. Later concept 2 may be better approach for individual since "Boil and Bite" portion requires to be replaced every six months to preserve the bite. For individual, the second concept eliminates to buy whole unit, they must only buy a "boil and bite" portion, when needed, saving money.

Figure 14C:
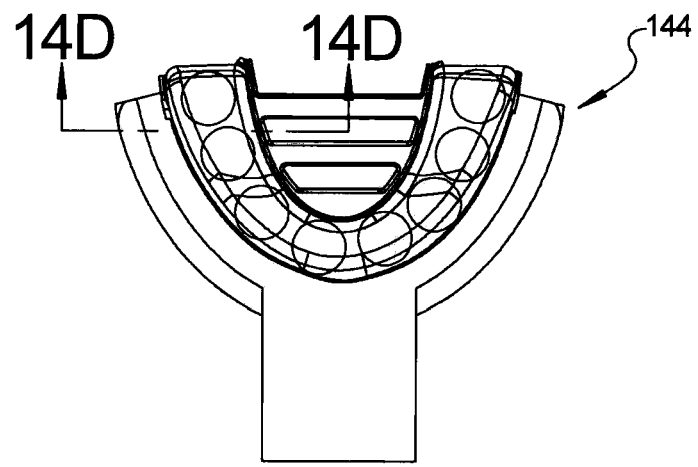
Figure 14A:
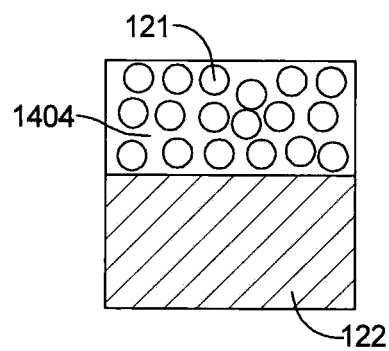

FIGS. 14A-14D show a customized, single piece, micro oral PAP device 144 manufactured by micro-cellular foaming injection molding. Device 144 illustrates a concept for temporarily customizing device 144 during sleep, allowing good grip by teeth and increasing comfort level. As shown in FIG. 14A, a soft material 121 is used for the portion of the device 144 touching the teeth which is made out of microcellular foam 1400. The microcellular foam 1404 can be open cell structure with regular elastomeric polymer or closed cell structure with highly elastomeric material. Soft material 121 may alternatively comprise polymeric gel material.

Figure 14B:
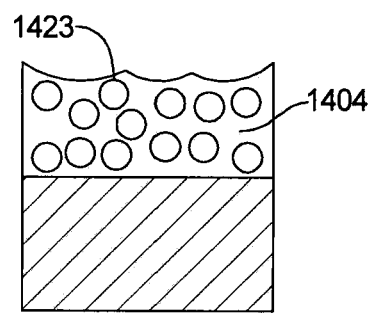
Figure 14D:
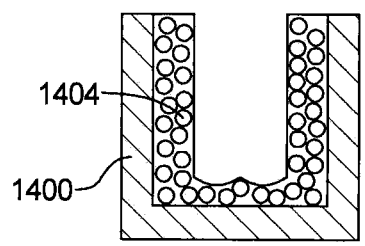

As shown in FIG. 14B, the individual inserts the device 144 in the mouth, and upon biting on the device, the applied pressure deforms the elastomeric structure of microcellular foam 1404, allowing the impression of teeth on the inside 1423 of the soft microcellular foam 1404. This way, device 144 stays in place during sleep. To take device 144 out from mouth upon waking up, the individual has to apply vertical downward force on device 144. Once device 144 is removed from the individual's mouth, the microcellular foam 1404 returns to its original shape and is ready for the next night to again form a customized device. FIG. 14C shows device 144 with microcellular foam 1404, while FIG. 14D depicts cross section A-A of a portion of upper arch 1400 showing the microcellular foam 1404 taking the shape of the individual's teeth after bite.

FIG. 15 depict a single step manufacturing method for hollow device by injecting material in two cavities, cavities rotation, followed by injecting plastic at intersection of two halves, creating hollow part.

FIG. 16 depicts micro-holes in the hollow tube (or hollow passage way), blowing air at very low flow rate, but stimulating the tongue to stay forward original position (does not allow to fall back) during sleep. These micro-holes can be near the tongue (lingual area) FIG. 16A and/or at the end of throat area (oropharynx area) as shown in FIG. 16B.

FIG. 16B depicts micro holes in the hollow tube at end connected to two side tubes of an arch, directing the air flow at the end of oropharynx (directly at throat region). This can significantly help in keeping airway open compared to providing airflow by just two sides tubes.

FIG. 17 depicts special microchip embedded into mouthguard for nerve stimulation. FIG. 18 depicts device as an impact sport guard with additional airflow during play and protection of teeth. Energy absorbing and dissipation away from the teeth is achieved by selecting right plastic material and internal design of the part wall like honeycomb or lattice like structure. This embodiment is referred to herein as a positive airway pressure impact sports guard with or without micro-blower(s).

FIG. 19 depicts the device as a sleep apnea diagnostic device to detect OSA, having various sensors located in the hollow housing and/or the maxillary or mandibular arches which would be capable of measuring and recording key data and proprietary algorithms providing AHI index which could be correlated to standard Sleep diagnostic tests such as PSG or PG.

Rigid or semi-rigid plastic examples suitable for use in manufacturing the devices include, but are not limited to: Commodity thermoplastics such as polyvinyl chloride, polyolefin and polystyrene: polyvinyl chloride having properties such as but not limited to: density of 1.2 to 1.4 g/cc, tensile strength in range of 40 to 55 Mpa, tensile elongation in range of 20 to 100%, flexural modulus in range of 2.0 to 5 GPa; polyolefin such as polyethylene and polypropylene materials having properties such as but not limited to: density in range of 0.86 to 0.98 g/cc, tensile strength in range of 20 to 60 Mpa, tensile elongation in range of 50 to 150%, flexural modulus in range of 1.5 to 2.0 GPa, notched impact strength in range of 50 to 200 J/m; polycarbonate having properties such as but not limited to: density of 1.2 g/cc+/−0.1, tensile strength in range of 50 to 85 Mpa, tensile elongation in range of 40 to 140%, flexural modulus in range of 2.0 to 2.6 GPa, impact strength in range of 300 to 1000 J/m; acrylics such as polymethyl methacrylate (PMMA), acrylic copolymers and acrylic multipolymer blends having properties such as but not limited to: density in range of 1.1 to 1.2 g/cc, tensile strength in range of 30 to 75 Mpa, tensile elongation in range of 4 to 30%, flexural modulus in range of 1.5 to 4.0 GPa, notched impact strength in range of 100 to 300 J/m; Rigid thermoplastics polyurethanes (TPU) can be polyester, polycarbonate or polyether based TPU having properties such as but not limited to: density with the range of 1.05 g/cc to 1.20, shore D hardness of 35 D to 85 D, tensile strength @ break 35 to 70 MPa, tensile elongation in range of 50 to 300%, flexural modulus in range of 0.5 to 2.5 GPa; Polyesters including PBT or PET having properties such as but not limited to: density in range of 1.2 to 1.4 g/cc, tensile strength @ break in range of 40 to 70 Mpa, tensile elongation in range of 40 to 100%, flexural modulus in range of 2.0 to 3.5 GPa, notched impact strength in range of 35 to 70 J/m; ABS having properties such as but not limited to: density in range of 1.00 to 1.05 g/cc, tensile strength @ break in range of 30 to 50 Mpa, tensile elongation in range of 5 to 30%, flexural modulus in range of 2.0 to 3.0 GPa, notched impact strength in range of 250 to 350 J/m; Nylons or polyamides such as PA 6, PA 66, PA 11, PA 12, PA 46, PA 610, having properties such as but not limited to: density in range of 1.00 to 1.2 g/cc, tensile strength @ break in range of 45 to 85 Mpa, tensile elongation in range of 30 to 200%, flexural modulus in range of 1.0 to 3.0 GPa, notched impact strength in range of 25 to 120 J/m; Polyether ether ketone (PEEK) having properties such as but not limited to: density in range of 1.30 to 1.35 g/cc, tensile strength @ break in range of 90 to 150 Mpa, tensile elongation in range of 10 to 40%, flexural modulus in range of 4.0 to 4.5 GPa, notched impact strength in range of 55 to 65 J/m; Composites of above plastics with glass fiber, carbon fiber and other fillers polymeric alloys comprising blends of polymers such as polycarbonate alloys with polybutylene terephthalate (PBT), and polyethylene terephthalate (PET) for improved chemical resistance, PC/ABS copolymer alloys for ease of processability, PC/TPU, PC/ABS, PC/SMA, PBT/PET/ASA alloys, PA/TPU and several combinations of all the plastics described above; thermosets comprising photopolymers made out of methacrylated oligomers, monomers, acrylated monomers, low molecular weight polymers or elastomers to reduced brittleness having properties such as but not limited to: density in range of 1.10 to 1.20 g/cc, tensile strength @ break in range of 40 to 65 Mpa, tensile elongation in range of 10 to 40%, flexural modulus in range of 2.0 to 4.0 GPa, notched impact strength in range of 10 to 40 J/m and shore D hardness of 50 to 80 D; Soft and elastomeric plastics include, but are not limited to: soft polyurethanes, EVA (ethylene vinyl acetate), TPE such as SEBS, elastomeric nylons, silicones elastomers, biopolymers (PLA—polylactic acid), thermoplastics or thermoset elastomers.

The devices can be formed of copolyester produced when more than one diacid or diol is used in the polyester polymerization process, such as PETG (polyethylene terephthalate glycol), PCTG (Polycyclohexylene dimethylene terephthalate glycol) with properties such as but not limited to: density in range of 1.2 to 1.7 g/cc, tensile strength @ break in range of 25 to 30 Mpa, Tensile elongation in range of 110 to 300%, flexural modulus in range of 1.8 to 2.2 GPa, notched impact strength in range of 100 J/m to no break; soft polyurethanes (TPU elastomers) having properties such as but not limited to: density with the range of 1.05 g/cc to 1.30, shore D hardness of 30 D to 75 D, tensile strength @ break 15 to 50 MPa, tensile elongation in range of 300 to 800%, flexural modulus in range of 0.03 to 0.15 GPa. compression set 10 to 45%, tear strength 80 to 180 N/mm; EVA (ethylene vinyl acetate) having properties such as but not limited to: density with the range of 0.93 g/cc to 0.96 g/cc, shore D hardness of 30 D to 50 D, tensile strength @ break 3 to 35 MPa, tensile elongation in range of 300 to 800%, elastic modulus in range of 0.015 to 0.08 GPa; and silicones elastomers having properties such as but not limited to: density with the range of 1.12 g/cc to 1.2 g/cc, shore A hardness of 30 A to 70 A, tensile strength @ break 8 to 15 MPa, tensile elongation in range of 300 to 800%, compression set 10 to 20%, tear strength 30 to 40 N/mm.

Additionally, the material can be formed of TPE such as SEBS having properties such as but not limited to: density with the range of 1.15 g/cc to 1.25 g/cc, shore D hardness of 35 D to 75 D, tensile strength @ break 10 to 45 MPa, tensile elongation in range of 200 to 375%, compression set 5 to 30%, tear strength 80 to 100 N/mm. Polymeric materials can also be blended with fillers such as carbon fibers, carbon nanotubes, glass microsphere, silica, etc., to obtain the desired properties of a mouth guard.

The invention relates to oral or nasal or a combination of oral and nasal sleep apnea diagnostic device as Home Sleep Testing (HST) device for the diagnosis of obstructive sleep apnea (OSA) and snoring; having microprocessors and sensors, comprising of following configurations: 1) Basic HST unit for standard OSA testing. This configuration without mandibular advancement (MAD) can be provided with upper mouth piece only (i.e. without the lower mouth piece) or with lower mouth piece only (i.e. without the upper mouth piece); 2) HST unit with mandibular advancement (MAD)—this is to validate specific mandibular advancement setting and treatment of sleep apnea with or without innovative oral CPAP sleep apnea device or current CPAP device; 3) HST unit to be used in conjunction with current CPAP for determining the efficacy of a pressure setting; 4) HST device as sleep apnea diagnostic as well as treatment device: In addition to device performing as diagnostic tool (as Home Sleep Testing (HST) or Out of center Sleep Testing (OOCST) for detecting OSA, the same device can also be used as sleep apnea treatment and/or anti-snoring device.

The device can be fitted with a mix of sensors to measure air flow; SpO2 (oxygen saturation in blood), heart rate (beats/min) and respiratory effort. These parameters would be sufficient to perform a sleep study conforming to the guidelines by CMS or AASM for a Type III or Type iV study. Additional sensors can be included to measure temperature; body positions while at sleep, Sound (breathing) variation and snoring, Single channel ECG (heart), EEG for brain activity etc. Actual sleep time is not measured by current HST devices while in one embodiment the device can have built-in sensors or wirelessly communicating sensors like heart rate, breathing monitoring, position sensor for body movement during sleep, temperature along with proprietary algorithm helps in measuring actual (true) sleep time which is very important for accurate (true) AHI number, a measure of severity of sleep apnea.

In one embodiment, the device would be fitted with a differential pressure sensor to measure airflow and pressure (or alternately with a PVDF calibrated strip), a novel pulse ox sensor from lips for oxygen saturation and heart rate (alternately could be a standard pulse oximeter with Bluetooth capability), and a photophlethysmographic (PPG) sensor to measure respiratory effort (alternately could be a standard RIP belt to acquire the same parameter).

All these parameters can be continuously acquired and stored on a memory SD card built into the unit (device) or wirelessly transferred using Bluetooth, wifi, cloud or other similar technologies to a mobile device or to cloud based server. This data can then be analyzed by automated computer algorithms for episodes of breathing irregularities while sleeping—such as apneaic or hypopneaic events and summarized to provide AHI/RDI information. The RDI is defined as the average number of respiratory disturbances. The device can be controlled wirelessly using mobile devices.

In another embodiment, the device can be enhanced by addition of sound sensor to measure breathing patterns and snoring variation, thermistor for temperature of air flow and breathing pattern, miniature video camera mounted on the mouthguard to take pictures of inside of mouth during sleep and a processing unit to capture and analyze these parameters to provide a far more comprehensive sleep study report compared to a Type III or Type IV HST device.

Both of above embodiments can be adapted to validate Mandibular Adjustment (MAD) setting by providing oral component with mandibular adjustments (lower jaw advancement) in specific fine increments. Also the device of present invention can be concurrently used with CPAP and validate efficacy of pressure setting for the CPAP treatment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms.

These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

In the foregoing description, the teachings have been described with reference to specific exemplary embodiments thereof. It will be apparent to those skilled in the art that a person understanding these teachings may conceive of changes or other embodiments or variations, which utilize the principles of this teachings without departing from the broader spirit and scope of the teachings. The specification and drawings are, therefore, to be regarded in an illustrative rather than a restrictive sense.

What is claimed is:

1. An oral sleep apnea treatment device selectively engagable with a patient's lips and teeth, said oral sleep apnea treatment device comprising:
   a front hollow housing defining a first through passage, said front hollow housing having an exterior surface configured to engage the patient's lips;
   a mouthpiece having an exterior surface defining a tooth engaging surface and defining second and third through passages, each defining an aperture disposed adjacent to the adjacent to the retromolar pad members when engaged with the patient's teeth, the front hollow housing being selectively engageable to the mouthpiece; and
   one of a pressure generating device and an air flow generating device disposed within the first through passage, the generating device configured to create an airflow through the second and third passage and adjacent the retromolar pad members.

2. The device of claim 1, wherein the device comprises a battery disposed within the front hollow housing, said battery being electrically coupled to the generating device.

3. The device of claim 1, wherein the device comprises a controller configured to regulate electrical power supplied to the generating device.

4. The device of claim 1, wherein the mouthpiece is formed using one of additive manufacturing, injection molding, thermoforming and blow molding.

5. The device of claim 4 wherein the mouthpiece is injection over-molding with an elastically deformable, low durometer material.

6. The device of claim 1, wherein the mouthpiece defines an aperture configured to project moving air onto an oropharynx area of the patient.

7. The device of claim 1, further comprising first and second members having member defining a u-shape, said first and second members defining the defining second and third through passages, and a plurality of flanges disposed between the first and second members and said plurality of flanges engaging a tongue.

8. The device of claim 1, the mouth piece comprises first and second u shaped components, the first and second u-shaped members defining the second and third through passages.

9. The device of claim 8, wherein the plurality of sensors comprise at least one of a pressure sensor, an airflow sensor, temperature sensors, sound sensor, an accelerometer, and a pulse oximeter.

10. The device of claim 8, wherein the control module comprises one of a closed loop control system and a wireless communication module.

11. The device of claim 1, further comprising a control module in the front hollow housing, wherein the control module is coupled to a plurality of sensors, the control module configured to provide a signal to control operation of the generating device.

12. The device of claim 1 further comprising a mandibular advancement device.

13. The device of claim 1 further comprising a nostril tubes in connection to the front hollow housing to a nasal passage.

14. An oral sleep apnea treatment device selectively engagable with a patient's lips and teeth, said oral sleep apnea treatment device comprising:
   a front hollow housing defining a first through passage, said front hollow housing having an exterior surface configured to engage the patient's lips;
   a mouthpiece having an exterior surface defining a tooth engaging surface and defining second and third through passages, each defining a plurality of apertures disposed adjacent to soft tissues within the patient's mouth when engaged with the patient's teeth, the front hollow housing being selectively engageable to the mouthpiece; and
   a blower disposed within the first through passage, the blower configured to create an airflow through the second and third passage and onto the patient's soft tissue.

15. The device of claim 14 further comprising electrodes configured to engage the soft palates and tongue.

16. The device of claim 14 further comprising a tilt sensor configured and a feedback mechanism, the feedback mechanism configured to wake the patient when the patient is not sleeping on a patient's side.

17. The device of claim 14 wherein the mouthpiece a boil and bite material.

18. The device of claim 14 wherein the plurality of apertures disposed adjacent to soft tissues within the patient's mouth are configured to blow air at very low flow rate, the micro-holes positioned adjacent a patients lingual area.

19. The device of claim 14 comprising a controller and a plurality of sensors disposed within in the front hollow housing, the controller being configured to calculate an AHI index.

20. The device of claim 19, wherein the plurality of sensors comprise one of a pressure sensor, an airflow sensor and one or more temperature sensors, sound sensor, tilt sensor, and a pulse oximeter.

* * * * *